US007374890B2

(12) United States Patent
Leonard et al.

(10) Patent No.: US 7,374,890 B2
(45) Date of Patent: May 20, 2008

(54) METHODS FOR IDENTIFYING COMPOUNDS THAT MODULATE ΔTRα2 ACTIVITY

(75) Inventors: Jack L. Leonard, Shrewsbury, MA (US); Alan P. Farwell, West Boylston, MA (US)

(73) Assignee: University of Massachusetts, Boston, MA (US)

( * ) Notice: Subject to any disclaimer, the term of this patent is extended or adjusted under 35 U.S.C. 154(b) by 441 days.

(21) Appl. No.: 10/822,591

(22) Filed: Apr. 12, 2004

(65) Prior Publication Data

US 2004/0265918 A1 Dec. 30, 2004

Related U.S. Application Data

(63) Continuation of application No. 09/894,734, filed on Jun. 28, 2001, now Pat. No. 6,730,472.

(60) Provisional application No. 60/214,572, filed on Jun. 28, 2000.

(51) Int. Cl.
*G01N 33/50* (2006.01)
*G01N 33/53* (2006.01)
*G01N 33/566* (2006.01)
*G01N 33/567* (2006.01)
*G01N 33/68* (2006.01)

(52) U.S. Cl. ....................... 435/7.1; 435/7.2; 435/7.21; 436/501

(58) Field of Classification Search ..................... None
See application file for complete search history.

(56) References Cited

U.S. PATENT DOCUMENTS 5,650,550 A 7/1997 Korach et al.

OTHER PUBLICATIONS

Auf'mkolk et al., "Antihormonal Effects of Plant Extracts: Iodothyronine Deiodinase of Rat Liver is Inhibited by Extracts and Secondary Metabolites of Plants," *Hormone Metab. Res.* 16:188-192 (1984).

Auf'mkolk et al., "Crystal Structure of Phlorizin and the Iodothyronine Deiodinase Inhibitory Activity of Phloretin Analogues," *Biochem. Pharmacol.* 35:2221-2227 (1986).

Auf'mkolk et al., "Inhibition of Rat Liver Iodothyronine deiodinase," *J. Biol. Chem.* 261:11623-11630 (1986).

Burris et al. "A nuclear hormone receptor-associated protein that inhibits transactivation by the thyroid hormone and retinoic acid receptors" *Proc. Natl. Acad. Sci. USA* 92:9525-9529 (1995).

Chassande et al. "Identification of Transcripts Initiated from an Internal Promoter in the c-erbAα Locus That Encode Inhibitors of Retinoic Acid Receptor-α and Triiodothyronine Receptor Activities" *Molecular Endrocrinology* 11, 9:1278-1290 (1997).

Chassande et al., "Identification of transcripts initiated from an internal promoter in the c-erbA alpha locus that encode inhibitors of retinoic acid receptor-alpha and triiodothyronine receptor activities," *Mol. Endrocrinol.* 11:1278-1290 (1997).

Cody et al., "Structure-Activity Relationships of Flavonoid Deiodinase Inhibitors and Enzyme Active-Site Models," *Prog. Clin. Biol. Res.* 213:373-382 (1986).

Farwell et al., "Degradation and recycling of the substrate binding subunit of type II iodothyronine 5'-deiodinase in astrocytes," *J. Biol. Chem.* 271:16369-16374 (1996).

Farwell et al., "Dissociation of Actin Polymerization and Enzyme Inactivation in the Hormonal Regulation of Type II Iodothyronine 5'-Deiodinase Activity in Astrocytes," *Endocrinol.* 131:721-728 (1992).

Farwell et al., "Identification of a 27-kDa Protein with the Properties of Type II Iodothyronine 5'—Deiodinase in Dibutyryl Cyclic AMP-simulated Glial Cells," *J. Biol. Chem.* 264:20561-20567 (1989).

Farwell et al., "The actin cytoskeleton mediates the hormonally regulated translocation of type II iodothyronine 5'-deiodinase in astrocytes," *J. Biol. Chem.* 265:18546-18553 (1990).

Farwell et al., "Thyroxine targets different pathyways of internalization of type II iodothyronine 5'deiodinase in astrocytes," *J. Biol. Chem.* 268:5055-5062 (1993).

Fraichard et al., The T3Rα gene encoding a thyroid hormone receptor is essential for post-natal development and thyroid hormone production, *The EMBO Journal* 16:4412-4420 (1997).

Gauthier et al., "Different functions for the thyroid hormone receptors TRα and TRβ in the control of thyroid hormone production and post-natal development," *The EMBO Journal* 18:623-631 (1999).

Göthe et al., "Mice devoid of all known thyroid hormone receptors are viable but exhibit disorders of the pituitary-thyroid axis, growth, and bone maturation," *Genes & Development* 13:1329-1341 (1999).

Horowitz et al., "Characterization of the domain struction of chick c-erbA by deletion mutation: in vitro translation and cell transfection studies," *Mol. Endocrinol.* 3:148-156 (1989).

Koehrle et al., "Iodothyronine Deidonase is Inhibited by Plant Flavonoids," *Prog. Clin. Biol. Res.* 213:359-371 (1986).

Koehrle et al., "Rat Liver Iodothyronine Monodeiodinase," *J. Biol. Chem.* 261:11613-11622 (1986).

Kolodny et al., "Studies of nuclear 3,5,3'-triiodothyronine binding in primary cultures of rat brain," *Endocrinology* 117:1848-1857 (1985).

Leonard et al., Cerebral cortex responds rapidly to thyroid hormones, *Science* 214:571-573 (1981).

Leonard et al., "Hormonal regulation of type II iodothyronine deiodinase in the brain," *Thyroid Hormone Metabolism: Molecular Biology and Alternate Pathways* (War & Visser eds.) CRC Press pp. 23-44 (1994).

(Continued)

*Primary Examiner*—Elizabeth C. Kemmerer
(74) *Attorney, Agent, or Firm*—Fish & Richardson P.C.

(57) ABSTRACT

Truncated thyroid hormone receptors ΔTRα1 and ΔTRα2 have been discovered to play a role in actin-based endocytosis, e.g., in the nervous system. The invention relates to methods of discovering ligands effective in modulating endocytosis and transgenic mice with altered expression of ΔTRα1 and ΔTRα2. The invention is useful for the discovery and testing of compounds for treating disorders of the nervous system such as depression.

21 Claims, 6 Drawing Sheets

OTHER PUBLICATIONS

Leonard et al., "Iodothyronine 5'-Deiodinase from Rat Kidney: Substrate Specificity and the 5'-Deiodination of Reverse Triiodothyronine," *Endocrinol.* 107:1376-1383 (1980).

Leonard et al., "Regulation of type II iodothyronine 5'-deiodinase by thyroid hormone. Inhibition of actin polymerization blocks enzyme inactivation in cAMP-stimulated glial cells," *Journal of Biological Chemistry* 265:940-946 (1990).

Leonard et al., "Thyroxine 5'-Deiodinase Activity of Rat Kidney: Observations on Activation by Thiols and Inhibition by Propylthiouracil," *Endocrinol.* 103:2137-2144 (1978).

Leonard, "Dibutryl cAMP induction of type II 5'deiodinase activity in rat brain astrocytes in culture," *Biochemical and Biophysical Research Communications* 151:1164-1172 (1988).

Rabie et al., "Analysis of the mechanisms underlying increased histogenetic cell death in developing cerebellum of the hypothyroid rat: determination of the time required for granule cell death," *Brain Res.* 190:409-414 (1980).

Safran et al., "Structural requirements of iodothyronines for the rapid inactivation and internalization of type II iodothyronine 5'-deiodinase in glial cells," *Journal of Biological Chemistry* 268:14224-14229 (1993).

Silva et al., "Regulation of Rat Cerebrocortical and Adenohypophyseal Type II 5'-Deiodinase by Thyroxine, Triiodothyronine, and Reverse Triiodothyronine," *Endocrinol.* 116:1627-1635 (1985).

Visser et al., "Different pathways of iodothyronine 5'-deiodination in rat cerebral cortex," *Biochem. Biophys. Res. Comm.* 101:1297-1304 (1981).

Visser et al., "Kinetic evidence suggesting two mechanisms for iodothyronine 5'-deiodination in rat cerebral cortex," *Proc. Nat. Acad. Sci. USA* 79:5080-5084 (1982).

Wikström et al., "Abnormal heart rate and body temperature in mice lacking thyroid hormone receptor $\alpha$1," *The EMBO Journal* 17:455-461 (1998).

Xiao et al., "Apoptosis in the developing cerebellum of the thyroid hormone deficient rat," *Front. Biosci.* 3:a52-57 (1998).

Laudet et al., "Genomic organization of the human thyroid hormone receptor alpha (c-erbA-1) gene," Nuc. Acids. Res. 19(5):1105-1112 (1991).

| | -OH | halide | isopropyl | OMe |
|---|---|---|---|---|
| R1 | ++ | ++ | ++ | ++ |
| R2 | ++ | | | |
| R3 | ++ | ++ | ++ | ++ |
| R4 | ++ | | | |
| R5 | ++ | | | |

```
                              SEQUENCE LISTING

<160> NUMBER OF SEQ ID NOS: 3

<210> SEQ ID NO 1
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 1

Tyr Ser Leu Ala Leu Glu Thr Ile Gln Ile Pro Ala Ser Leu Gly Leu
 1               5                  10                  15

Gly Phe Ile Ala Arg Val
            20


<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2

ggagactgtg gggtgtgg                                                    18


<210> SEQ ID NO 3
<211> LENGTH: 17
<212> TYPE: DNA
<213> ORGANISM: Artificial Sequence
<220> FEATURE:
```

-continued

```
<223> OTHER INFORMATION: Primer

<400> SEQUENCE: 3

ccagtgaatt cgagctc                                                  17
```

METHODS FOR IDENTIFYING COMPOUNDS THAT MODULATE ΔTRα2 ACTIVITY

CROSS-REFERENCE TO RELATED APPLICATION

This application is a continuation and claims the benefit of U.S. patent application Ser. No. 09/894,734, filed on Jun. 28, 2001, now U.S. Pat. No. 6,730,472, issued May 4, 2004, which claims the benefit of U.S. Provisional Patent Application Ser. No. 60/214,572, filed on Jun. 28, 2000, both of which are incorporated herein by reference in their entirety.

TECHNICAL FIELD

This invention relates to thyroid hormone receptors, and more particularly to non-nuclear effects of thyroid hormone.

BACKGROUND

Thyroid hormone (TH) has diverse effects on mammals, including effects on the neonatal and adult brain. In the developing animal, thyroid hormone regulates various events such as neuronal processing, glial cell proliferation, myelination, and neurotransmitter enzyme synthesis. The metabolically active form of thyroid hormone, 3, 5, 3'-triiodothyronine (T3), acts by binding to two receptors; TRα1 and TRβ1. These two receptors are encoded by the c-erbAα locus. Two truncated receptor transcripts have been identified that are also transcribed from the c-erbAα locus; ΔTRα1 and ΔTRα2 (Chassande et al., 1997, Mol. Endocrinol. 11:1278-1290). Neither truncated receptor has a DNA binding region and ΔTRα1 has been shown to antagonize T3-induced transcriptional activation.

Type II iodothyronine 5'-deiodinase (D2) is the key enzyme in the pathway that mediates the conversion of intracellular thyroxine (T4) to 3, 5, 3'-triiodothyronine (T3). D2 concentration can be mediated by thyroid hormone concentration and is regulated by enzyme inactivation. The D2 activity appears to be more sensitive to T4 than T3. The degradation of the enzyme is energy-dependent and apparently requires the structural integrity of the actin cytoskeleton, i.e., is regulated at least in part by actin-based endocytosis. p29 is the substrate binding subunit of D2. T4 induces inactivation of D2 and initiates the binding of p29 to F-actin. The bound p29 is transported to an endosomal pool followed by dissociation of the F-actin-p29 complex (Farwell et al., 1993, J. Biol. Chem. 268: 5055-5062).

SUMMARY

The present invention relates to the effects of thyroid hormone that are mediated by non-nuclear mechanisms. In particular, the invention relates to methods of identifying compounds that interact with a ΔTRα1 polypeptide and/or ΔTRα2 polypeptide (ΔTRα1; ΔTRα2). The invention also includes transgenic animals with altered or missing ΔTRα1 and ΔTRα2. Such animals are useful for identifying new targets for drug discovery.

Although ΔTRα1 and ΔTRα2 do not bind to 3, 5, 3'-triiodothyronine (T3), they do bind with high affinity to 3, 3', 5'-triiodothyronine (reverse T3; rT3) and that binding can be displaced by thyroxine (T4) and rT3 (Example 2). The invention relates to the discovery that the association of myosin V with p29 vesicles is dependent on thyroid hormone, e.g., T4 and rT3, bound to a ΔTRα2, and that stable complexes between p29, several synaptic vesicle proteins and myosin V can be isolated on actin fibers. Thus, T4, rT3, and certain analogs are useful for regulating actin-based endocytosis, especially movement of synaptic vesicles.

The invention features a method of assaying the functionality of a translation product of a mutant ΔTRα2 gene in a cell. The method includes binding a labeled ligand for a ΔTRα2 polypeptide to the translation product in a cell and measuring the amount, location, or rate of transit of the ligand in the cell. An increase in the amount, location, or rate of transit of the ligand in the cell compared to that in a cell that does not comprise a mutant ΔTRα2 gene indicates an increase in functionality of the translation product. A decrease in the amount location, or rate of transit of the ligand in the cell compared to a cell that does not comprise a mutant ΔTRα2 gene indicates a decrease in the functionality of the translation product. The ligand can be, e.g., a flavone, an aurone, or a T4 analog.

The invention includes an inhibitor of ΔTRα2 expression or activity. The inhibitor can be, e.g., a flavone, an aurone, or a T4 analog.

The invention also features a method of identifying a candidate compound that modulates ΔTRα2 activity by obtaining a ΔTRα2 polypeptide, contacting the ΔTRα2 with a test compound, assaying for binding of the test compound to ΔTRα2, such that binding indicates that the test compound that binds to the ΔTRα2 polypeptide is a candidate compound that modulates ΔTRα2 activity. The test compound can be, e.g., a flavone, an aurone, or a T4 analog.

In another aspect, the invention provides a method of identifying a candidate compound that modulates ΔTRα2 activity. This method includes obtaining a ΔTRα2 polypeptide bound to a ΔTRα2 ligand, contacting the ΔTRα2 bound to the ΔTRα2 ligand with a test compound, and measuring the displacement of the ΔTRα2 ligand from the ΔTRα2 polypeptide, such that displacement indicates that the a test compound is a candidate compound that modulates ΔTRα2 activity. The test compound can be, e.g., a flavone, an aurone, or a T4 analog.

The invention also includes a method of identifying a candidate compound that modulates ΔTRα2 activity. This method includes the steps of obtaining a test sample containing a ΔTRα2, incubating the test sample with a test compound, and assaying the test sample containing the test compound for an alteration in type II 5' deiodinase (D2) activity, such that a test compound that alters D2 activity when compared to a test sample that was not incubated with the test compound is a candidate compound. In this method, the test compound may decrease the amount of D2 activity. The test compound can be, e.g., a flavone, an aurone, or a T4 analog.

The invention also features a method of identifying a candidate compound that modulates ΔTRα2 activity which includes the steps of obtaining a test sample containing a ΔTRα2, performing an actin binding assay with the test sample in the presence of a test compound, such that a test compound that alters the binding of p29 vesicles to F-actin when compared to a test sample that was not incubated with the test compound is a candidate compound. The test compound can be, e.g., a flavone, an aurone, or a T4 analog.

The invention includes a compound identified by the any of the methods described above. The invention also includes an inhibitor of ΔTRα2 expression or activity.

Other aspects of the invention are methods of treating a subject who has a neurologic disorder or a psychiatric disorder (e.g., a mood disorder or depression) by administering to the subject a therapeutically effective amount of a ΔTRα2 ligand.

The invention also features an isolated nucleic acid molecule that includes a ΔTRα2 targeting construct that contains a DNA sequence homologous to sequences encoding a mouse ΔTRα2, such that when the construct is introduced into a non-human animal (e.g., a mouse) cell or an ancestor of the animal cell at an embryonic stage, and the construct-derived sequences are incorporated into an endogenous TRα gene, the cell does not express ΔTRα2 in significant amounts (e.g., not more than 75%, 50%, 25%, 10%, or 5% of the level of expression in a cell or animal having a wild type gene). The invention includes a vector containing this nucleic acid. The construct can contain a nucleic acid sequence that is homologous to intron 7 of a mouse TRα gene or a nucleic acid sequence that is homologous to exon 10 of a mouse TRα DNA sequence. In some aspects of the invention, introduction of the construct into the cell disrupts the AP1, ctf, GR, SP1, or ets1 sequence of intron 7. The isolated nucleic acid molecule can also include a gene selection cassette.

The invention features a transgenic, non-human animal whose germ cells and somatic cells include a mutated TRα gene, the mutation being sufficient to inhibit binding of thyroxine (T4) to ΔTRα2 transcribed from the gene. The mutated gene is introduced into the non-human animal or an ancestor of the animal at an embryonic stage, such that the animal, if homozygous for the mutation, has impaired motor function. The non-human animal can be a mouse, a rat, a goat, a sheep, or a pig. The invention includes a cell derived from the transgenic animal. The cell can be an astrocyte or other neuronal cell type. In such transgenic animals, the TRα gene can be mutated in intron 7 or in exon 10.

Another aspect of the invention features a transgenic non-human animal whose somatic and germ cells include a disrupted TRα gene, the disruption being sufficient to inhibit the binding of T4 to a ΔTRα1 or ΔTRα2 translation product of the TRα gene and the disrupted gene was introduced into the animal or an ancestor of the animal at an embryonic stage. Such an animal, if homozygous for the disrupted gene, has impaired motor function. The animal can be a rodent (e.g., a mouse or a rat), a goat, a pig, or a sheep. The disruption in such an animal can include a mutation in intron 7 or exon 10 of the TRα gene. The disruption can include a deletion of all or a part of intron 7 of the TRα gene or a deletion of all or part of exon 10 of the TRα gene.

A "transgene" is any piece of DNA that is inserted by artifice into a cell, and becomes part of the genome of the organism that develops from that cell or progeny of the organism. Such a transgene may include a gene that is partly or entirely heterologous (i.e., foreign) to the transgenic organism, or may represent a gene or part of a gene that is homologous with an endogenous gene of the organism.

A cell that is "transgenic" is one which includes a DNA sequence inserted by artifice into a cell to become part of the genome of the organism which develops from that cell or progeny of the organism. As used herein, the transgenic organism can be an animal, generally a mammal (e.g., a rodent such as a mouse or rat), and the DNA (transgene) is inserted into the nuclear genome.

A "transgenic animal" is an animal which includes a transgene. In general, the transgene is inserted into an embryonal cell and becomes a part of the genome of the animal which develops from that cell, or an offspring of such an animal. The transgene may introduce a heterologous DNA sequence into the embryonal cell or introduce an alteration such as a deletion, insertion, or substitution of an endogenous DNA sequence (e.g., by homologous recombination). In the transgenic animals described herein, the transgene causes cells to express an altered form of ΔTRα1 or ΔTRα2. Such animals include those produced using methods such as homologous recombination. In general, the animals produced by the transgenic technology of the invention are mammals although any animal that can be produced by such technology is encompassed by the invention. Mammals used for the invention include non-human primates, sheep, goats, horses, cattle, pigs, rabbits, and rodents such as guinea pigs, hamsters, rats, gerbils, and mice.

As used herein, a "homologously recombinant animal" is a non-human animal, e.g., a mammal, such as a mouse, in which an endogenous gene has been altered by homologous recombination between the endogenous gene and an exogenous DNA molecule introduced into a cell of the animal, e.g., an embryonic cell of the animal, prior to development of the animal.

A "ΔTRα1 ligand" or "ΔTRα2 ligand" is a compound that binds to a ΔTRα1 or ΔTRα2, respectively. In some embodiments such a ligand binds to a ΔTRα1 or ΔTRα2 with an affinity of greater than or equal to $10^{-8}$ Mol/L.

A molecule that "specifically binds" is a molecule that binds to a particular entity, e.g., a ΔTRα1 or ΔTRα2, but which does not substantially recognize or bind to other molecules in a sample, e.g., a biological sample, which includes that particular entity, e.g., a ΔTRα1 or ΔTRα2.

The terms ΔTRα1 "candidate compound" or ΔTRα2 "candidate compound" refer to compounds that interact with or affect the activity of a ΔTRα1 or ΔTRα2. Such candidate compounds may be identified, e.g., by their ability to bind to one of the receptors, by their ability to displace a bound ligand from the receptor, by indirect assays such as ability to alter D2 activity when the candidate compound is incubated with the receptor in a D2-containing preparation, or by this ability to affect the association of myosin V with p29 vesicles. Candidate compounds may also be ligands.

A "test compound" is a compound used in the methods of the invention that is tested for its qualifications as a candidate compound.

A "homologous sequence" is a sequence with identity to a reference sequence. Calculations of homology (i.e., sequence identity) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, the length of a reference sequence aligned for comparison purposes (e.g., when aligning a second sequence to a ΔTRα1 or ΔTRα2 amino acid sequence) is at least 30%, 40%, 50%, 60%, 70%, 80%, or 90% of the length of the reference sequence. The length of the reference sequence can also be 100%. The reference sequence can be a full-length amino acid sequence of ΔTRα1 or ΔTRα2 or a partial sequence, e.g., a domain, intron, or exon (such as intron 7 or exon 10 of a mouse TRα sequence). In an embodiment, the length of a reference sequence aligned for comparison purposes (e.g., when aligning a second sequence to a ΔTRα1 or ΔTRα2 nucleic acid sequence) is at least 30%, 40%, 50%, 60%, 70%, 80%, or 90% of the length of the reference sequence. The length of the reference nucleic acid sequence can also be 100%. The reference sequence can be a full-length nucleic acid sequence encoding a ΔTRα1 or ΔTRα2 or a partial sequence, e.g., a sequence that codes for a domain, intron, or exon such as intron 7 or exon 10. For some purposes, e.g., homologous recombination, the nucleic acid sequence may be a genomic sequence (e.g., include intron sequences). The amino acid residues or nucleotides at corresponding amino acid positions or nucleotide positions are compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. Another set of parameters (e.g., that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences (such as human ΔTRα1, ΔTRα2, or myosin V amino acid or nucleic acid sequences). Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules useful in the invention (such as human ΔTRα1, ΔTRα2, or myosin V). BLAST protein searches can be performed with the XBLAST program, score=50, wordlength=3 to obtain amino acid sequences homologous to protein molecules useful in the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See www.ncbi.nlm.nih.gov.

The terms "sufficiently identical" or "substantially identical" are used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%. 91%, 92%, 93%, 94%, 95%, 96%, 97%, 98% or 99% identity are defined herein as sufficiently or substantially identical.

A mutant ΔTRα1 or ΔTRα2 gene encodes a ΔTRα1 or ΔTRα2 polypeptide that includes a change in comparison to the wild-type amino acid sequence. In general, these changes arise from genetic engineering (e.g., by transgenic methods). These changes also include naturally occurring mutations and alleles.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Among the advantages of the present invention are new methods of identifying candidate compounds that affect the non-nuclear effects of thyroid hormone, e.g., those involving ΔTRα1 and ΔTRα2. Such compounds may be useful in treatments for disorders that involve such non-nuclear effects. The present invention also provides methods of treatment for disorders of the nervous system and psychiatric disorders such as depression, e.g., with compounds that bind to ΔTRAl and ΔTRα2.

The details of one or more embodiments of the invention are set forth in the accompanying drawings and the description below. Other features, objects, and advantages of the invention will be apparent from the description and drawings, and from the claims.

Data are expressed as the percent maximal binding and are the means +/− SE of triplicate determinations.

Figure 10:
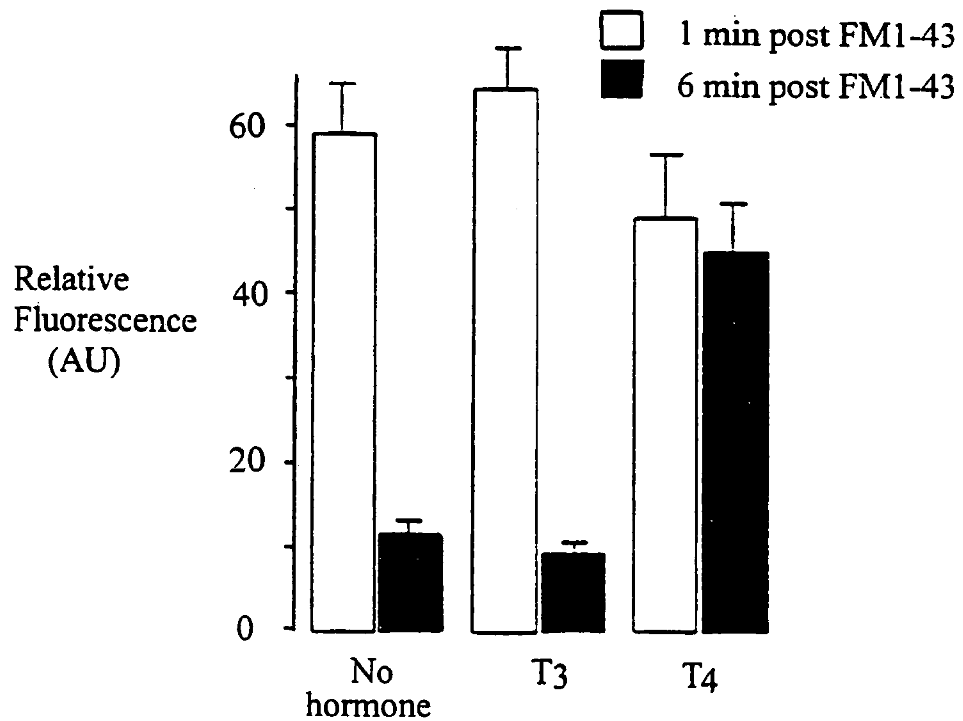

FIG. 10 is a graph illustrating the effects of acute T3 and T4 treatment on synaptic vesicle recycling in cerebellar granule neurons.

Figure 11A:
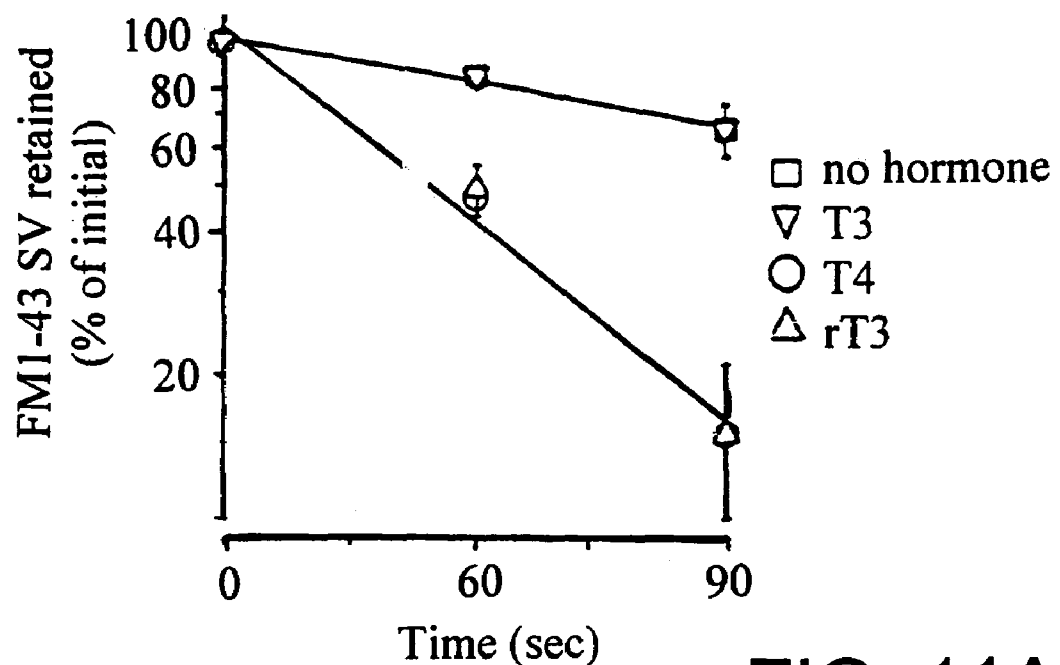
Figure 11B:
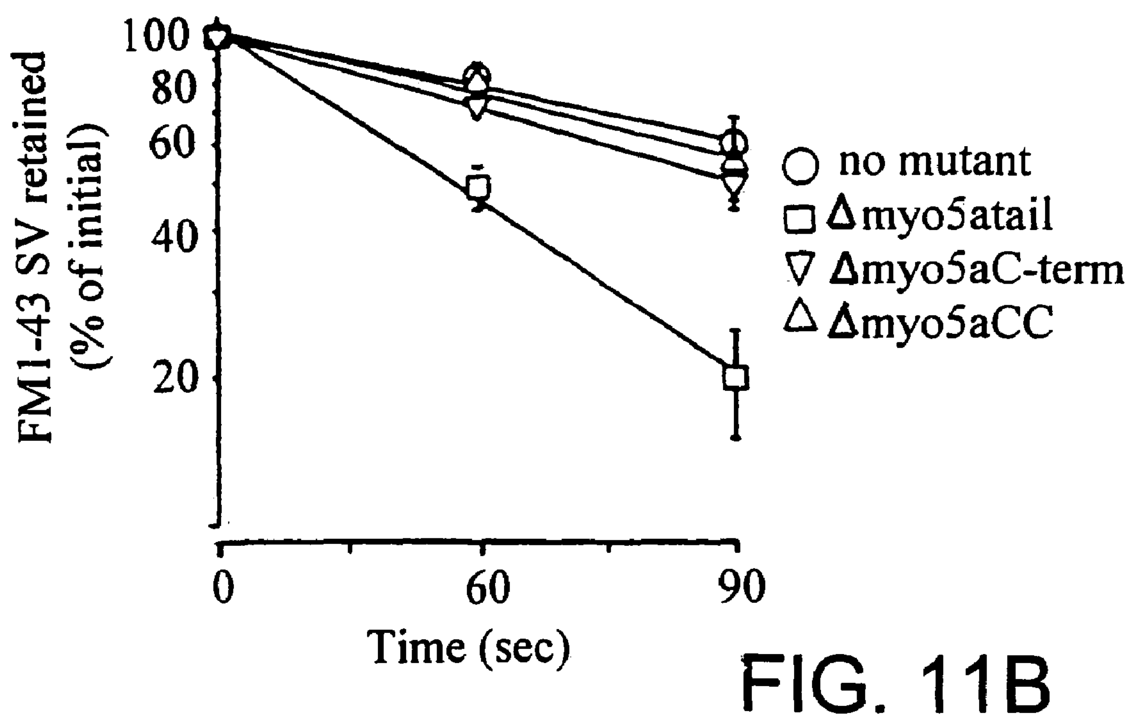

FIGS. 11A and 11B are graphs illustrating the rate analysis of the release of FMI-43-loaded synaptic vesicles from cerebellar granule neurons under continuous stimulus. FIG. 11A illustrates the results of experiments in cultured cerebellar granule neurons. FIG. 11B illustrates the results of experiments in cultured cerebellar granule neurons expressing mutant myo5a (mutant myosin V).

DETAILED DESCRIPTION

The present invention relates to the non-nuclear effects of thyroid hormone involving the truncated thyroid hormone receptors ΔTRα1 and ΔTRα2. In particular, the invention relates to methods of identifying compounds that bind to ΔTRα2 and are therefore useful, e.g., for treating disorders involving endocytosis, especially disorders of the nervous system and psychiatric disorders, for example, depression. The invention also involves methods of making transgenic animals and transgenic animals with altered ΔTRα1 and/or ΔTRα2. Such animals are useful, e.g., for identifying components of biochemical pathways involving ΔTRα1 and/or ΔTRα2, thus providing additional targets for drug discovery. The transgenic animals of the invention are also useful for testing ΔTRα1 and ΔTRα2 ligands for effects unrelated to receptor binding.

Synaptic vesicle recycling is a fundamental process that is central to continued synaptic transmission. Movement of recycling synaptic vesicles between the reserve and readily releasable pools in the nerve terminal is the principal means by which the neuron replenishes spent vesicles, removes defective vesicles, regulates the quantity of neurotransmitter available for release and insures maximal refilling of the recycling synaptic vesicles. The present invention relates to the discovery that T4 and its analogs are involved in the regulation of synaptic vesicle recycling through specific non-nuclear receptors, and that myosin V is a key molecular motor involved in this process. Thus, potential sites for pharmacological manipulation of synaptic vesicle availability are identified and can be used to identify compounds that modulate synaptic transmission.

Intron 7 of the thyroid hormone receptor gene contains an alternative transcriptional start site. The gene products of the alternative transcription are the truncated versions of the TRas (ΔTRas). ΔTRα1 is encoded by exons 8-9 resulting in an approximately 16 kd protein. ΔTRα2 is encoded by exons 8-10 resulting in an approximately 25 kd protein. The invention is based, in part, on the discovery that these truncated receptor forms specifically bind to T4 and rT3 (Example 2). Nucleic acid sequences that encode ΔTRα1 and ΔTRα2 are known for some species, e.g., Genbank No. X07409 (rat) and Genbank No. X07751 (mouse), respectively.

In experiments designed to identify molecules that are associated with a ΔTRα1 or ΔTRα2, ΔTRα2 was discovered to be associated with synaptic vesicles and to mediate thyroid hormone-dependent endocytosis via interactions with myosin V (Examples 2-4). This finding is important because it suggests that ΔTRα2 is associated with the regulation of endocytosis, e.g., re-uptake of neurotransmitters.

Based on the discoveries disclosed herein, it is shown that T4 can mediate endocytosis and vesicle transport and is thus involved in neurotransmitter re-uptake. In the absence of T4, there can be decreased re-uptake. Thus, T4, rT3, and analogs of these hormones may be useful for treating disorders associated with the nervous system, for example, modulation of neurotransmitter re-uptake. The invention therefore encompasses methods of identifying compounds that affect the thyroid hormone-mediated yesicle transport system (Example 6).

The invention also features transgenic animals that lack expression of a ΔTRα (Example 5), which are useful for identifying additional components of the vesicle transport system, providing additional novel drug targets.

Screening Assays for Compounds that Bind to or Modulate a ΔTRα1 or a ΔTRα2 Polypeptide One approach to identifying compounds that bind to a ΔTRα1 or a ΔTRα2 is to assay for compounds that interfere with the binding of a ΔTRα1 or a ΔTRα2 to a known binding partner (e.g., T4 or rT3). In one such method, interaction of a ΔTRα1 or ΔTRα2 with a ligand is monitored using methods described herein or by other methods known in the art. Ligands that interfere with such binding are candidate compounds.

Screening Assays

The invention provides methods (also referred to herein as "screening assays") for identifying modulators, i.e., candidate or test compounds or agents (e.g., peptides, peptidomimetics, small organic or inorganic molecules, carbohydrates, aptamers, or other drugs) that bind to a ΔTRα1 or a ΔTRα2 polypeptide or have a stimulatory or inhibitory effect on, for example, expression or activity of a ΔTRα1 or a ΔTRα2 polypeptide. In some cases it may be desirable to use more than one of the assays to confirm the effect of a compound, e.g., if a molecule is identified as a candidate compound using one assay, a second, different assay may be employed to confirm the efficacy of the candidate compound's potential for influencing vesicle transport.

In one embodiment, an assay is a cell-based assay in which a cell that expresses a synaptic vesicle-associated form of a ΔTRα2 or a biologically active portion thereof, is contacted with a test compound and the ability of the test compound to bind to the ΔTRα1 or ΔTRα2 determined. For example, the cell can be of animal, e.g., mammalian, origin. Determining the ability of the test compound to bind to the ΔTRα1 or ΔTRα2 can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled, for example with, horseradish peroxidase, alkaline phosphatase, or luciferase, and the enzymatic label detected by determination of conversion of an appropriate substrate to product. In another embodiment, the assay comprises contacting a cell which expresses a vesicle-associated form of a ΔTRα1 or a ΔTRα2 of the invention, or a biologically active portion thereof, on the cell surface with a known compound which binds to the ΔTRα1 or ΔTRα2 to form an assay mixture, contacting the assay mixture with a test compound, and determining the ability of the test compound to interact with the ΔTRα1 or ΔTRα2, by monitoring the ability of the test compound to preferentially bind to the ΔTRα1 or ΔTRα2 or a biologically active portion thereof as compared to the known compound.

In another embodiment, an assay is a cell-based assay comprising contacting a cell expressing a ΔTRα1 or ΔTRα2, or a biologically active portion thereof, with a test compound and determining the ability of the test compound to modulate (e.g., stimulate or inhibit) the activity of the polypeptide or biologically active portion thereof. The ability of the test compound to modulate the activity of the ΔTRα1 or ΔTRα2 or a biologically active portion thereof can be determined, for example, by confocal microscopy to assay alterations in synaptic vesicle transport within the cell in the presence of the test molecule compared to in the absence of the test molecule or in the presence of T4 or rT3.

The ability of a ΔTRα1 or a ΔTRα2 to bind to or interact with a target molecule can be determined by one of the methods described herein for determining direct binding. As used herein, a "target molecule" is a molecule with which a selected ΔTRα1 or ΔTRα2 binds to or interacts with in nature, for example, a T4 molecule, an F-actin, or other component of the vesicle recycling pathway (including structural components of a vesicle, e.g., a synaptic vesicle) with which a ΔTRα1 or a ΔTRα2 interacts in nature. The ability of a polypeptide of the invention to bind to or interact with a target molecule can be determined by monitoring the activity of the target molecule. For example, the activity of the target molecule can be determined by detecting an alteration in the activity of D2 (e.g., a decrease in D2 activity or expression in the presence of a T4 mimetic) or some other cellular response that is associated with binding to a ΔTRα1 or a ΔTRα2.

A cell-free assay can also be used to identify candidate compounds. In such an assay, a ΔTRα1 or a ΔTRα2 or biologically active portion thereof, is contacted with a test compound and the ability of the test compound to bind to the ΔTRα1 or ΔTRα2, or biologically active portion thereof is determined. Binding of the test compound to the ΔTRα1 or ΔTRα2 can be determined either directly or indirectly as described herein. In one embodiment, the assay includes contacting the ΔTRα1 or ΔTRα2 polypeptide or biologically active portion thereof, with a known compound that binds to the ΔTRα1 or ΔTRα2 to form an assay mixture, contacting the assay mixture with a test compound, and determining the ability of the test compound to interact with the ΔTRα1 or ΔTRα2, wherein determining the ability of the test compound to interact with the ΔTRα1 or ΔTRα2 comprises determining the ability of the test compound to preferentially bind to the ΔTRα1 or ΔTRα2 or biologically active portion thereof as compared to the known compound.

Another type of cell-free assay that can be used to identify candidate compounds comprises contacting a ΔTRα1 or ΔTRα2 polypeptide, or biologically active portion thereof with a test compound and the ability of the test compound to modulate (e.g., stimulate or inhibit) the activity of the ΔTRα1 or ΔTRα2 or biologically active portion thereof is determined. The ability of the test compound to modulate the activity of the ΔTRα1 or ΔTRα2 can be determined, for example, by measuring the ability of the ΔTRα1 or ΔTRα2 to bind to a target molecule by one of the methods described herein for determining direct binding. In an alternative assay, the ability of the test compound to modulate D2 activity can be determined.

A cell-free assay can be used for identifying a candidate compound in which a ΔTRα1 or ΔTRα2 polypeptide, or biologically active portion thereof, is contacted with a known compound that binds the ΔTRα1 or ΔTRα2 to form an assay mixture. The assay mixture is then contacted with a test compound, and the ability of the test compound to interact with the ΔTRα1 or ΔTRα2 (e.g., to displace the binding of the known compound) is determined. The ability of the test compound to interact with ΔTRα1 or ΔTRα2 indicates ability of the test compound to specifically bind to or modulate the activity of a target molecule.

In some of the cell-free assay methods of the present invention, it may be desirable to immobilize either the ΔTRα1 or ΔTRα2 or the target molecule components of the assay to facilitate separation of complexed from uncomplexed forms of one or both of the components, as well as to accommodate automation of the assay. Binding of a test compound to the ΔTRα1 or ΔTRα2, or interaction of the ΔTRα1 or ΔTRα2 with a target molecule in the presence and absence of a candidate compound, can be accomplished in any vessel suitable for containing the reactants. Examples of such vessels include microtitre plates, test tubes, and micro-centrifuge tubes. For this type of assay, a fusion protein can be provided that adds a domain that allows one or both of the proteins to be bound to a matrix. For example, glutathione-S-transferase (GST) fusion proteins or glutathione-S-transferase fusion proteins can be adsorbed onto glutathione Sepharose beads (Sigma Chemical; St. Louis, Mo.) or glutathione-derivatized microtitre plates, which are then combined with the test compound or the test compound and either the non-adsorbed target molecule or a ΔTRα1 or ΔTRα2, and the mixture incubated under conditions conducive to complex formation (e.g., at physiological conditions for salt and pH).

Following incubation, the beads or microtitre plate wells are washed to remove any unbound components and complex formation is measured either directly or indirectly, for example, as described above. Alternatively, the complexes can be dissociated from the matrix, and the level of binding or activity of the ΔTRα1 or ΔTRα2 can be determined using standard techniques.

Other techniques for immobilizing proteins on matrices can also be used in the screening assays of the invention. For example, a ΔTRα1, ΔTRα2, or target molecule can be immobilized utilizing conjugation of biotin and streptavidin. Biotinylated ΔTRα1, ΔTRα2, or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with a ΔTRα1, ΔTRα2 or a target molecule, but which do not interfere with binding of the ΔTRα1 or ΔTRα2 to a target molecule, can be derivatized to the wells of the plate, and unbound target or receptor (ΔTRα1 or ΔTRα2) trapped in the wells by antibody conjugation. Methods for detecting such complexes, in addition to those described above for the GST-immobilized complexes, include immunodetection of complexes using antibodies reactive with a ΔTRα1, ΔTRα2, or target molecule, as well as enzyme-linked assays which rely on detecting an enzymatic activity associated with the detecting antibody bound to ΔTRα1, ΔTRα2, or target molecule.

Modulators of expression of a ΔTRα1 or ΔTRα2 polypeptide are identified in a method in which a cell is contacted with a candidate compound and the expression of the selected mRNA or protein (i.e., the mRNA or protein corresponding to a ΔTRα1 or ΔTRα2, or a nucleic acid encoding a ΔTRα1 or ΔTRα2) in the cell is determined. The level of expression of the selected mRNA or protein in the presence of the candidate compound is compared to the level of expression of the selected MRNA or protein in the absence of the candidate compound. The candidate compound can then be identified as a modulator of expression of a ΔTRα1 or a ΔTRcc2 based on this comparison. For example, when expression of the selected MRNA or protein is greater (e.g., two-fold greater) in the presence of the candidate compound than in its absence, the candidate compound is identified as a stimulator of the selected MRNA or protein expression. Alternatively, when expression of the selected MRNA or protein is less (e.g., two-fold less) in the presence of the candidate compound than in its absence, the candidate compound is identified as an inhibitor of the selected mRNA or protein expression. Statistically significant differences (e.g., $p \leqq 0.05$) may be used as a means of determining whether there are significant differences in expression sufficient to indicate that a compound stimulates or inhibits expression. The level of the selected mRNA or protein expression in the cells can be determined by methods described herein.

D2 as a Marker in Screening Assays

The enzyme type II 5' deiodinase (D2) is a particularly useful marker for expression or activity of a molecule that affects ΔTRα1 or ΔTRα2 expression or activity as described herein. This is because D2 activity rises in the presence of T4 and therefore will rise in the presence of molecules that mimic the effects of T4 (e.g., rT3). Thus, D2 activity can be assayed in an appropriate system to determine whether a molecule has T4-like activity, e.g., is a candidate compound. D2 is especially useful as a marker of T4 or molecules with T4-like activity in in vivo assays. Such assays are known in the art and are described herein.

In an example of such an assay, a biological sample is sonicated in 50 mM HEPES (pH 7.0) containing 1 mM EDTA and 10 mM dithiothreitol (DTT). D2 activity is determined in the presence of 20 mM dithiothreitol and 1 mM 6-n-propylthiouracil. The ability of a test compound to modulate D2 expression or activity is compared to that of a known compound, for example, 2 nM $rT_3$ (Visser et al, 1982, Proc. Nat. Acad. Sci. USA 79:5080-5084).

Test/candidate Compounds

In one embodiment, the invention provides assays for screening test compounds to see if they bind to or modulate the activity of a ΔTRα1 or a ΔTRα2 or biologically active portion thereof and so are candidate compounds. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, 1997, Anticancer Drug Des. 12:145).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233. Molecular libraries are also available commercially from various sources.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869), or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

Candidate compounds that are especially useful in the invention include reverse T3 (rT3), T4, T4 analogs, and flavones (Auf'mkolk et al., 1986, J. Biol. Chem. 261:11623-30; Auf'mkolk et al., 1986, Biochem. Pharmacol. 35:2221-2227; Auf'mkolk et al., 1984, Hormone Metab. Res. 16:188-92; Cody et al., 1986, Prog. Clin. Biol. Res. 213:373-82; Koehrle et al., 1986, J. Biol. Chem. 261:11613-22; Koehrle et al., 1986, Prog. Clin. Biol. Res. 213:359-71) including aurones, phloretins, and isoflavones (including phytoestrogens).

Figure 1:
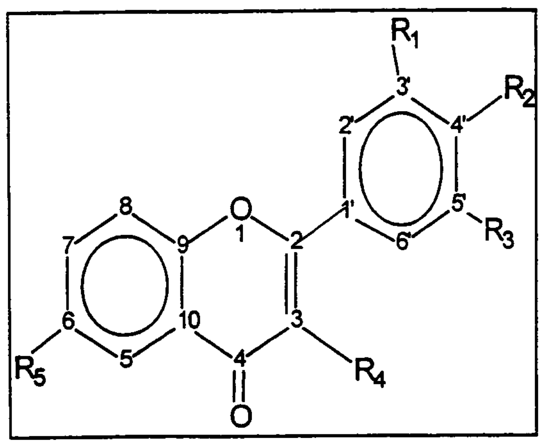
FIG. 1 is a schematic representation of the general structure of flavones and examples of structures of candidate compounds.

For example, the flavone EMD21388 and derivatives of EMD21388 are candidate compounds because the presence of EMD21388 can inhibit T4 deiodinases and can competitively block the binding of T4 to its serum binding partner, transthretin. In astrocytes, EMD21388 decreases the quantity of D2 activity as does T4. Because the invention is based on the discovery of the association between myosin V and ΔTRα2, flavone derivatives are likely to be potent ligands and effectors of the actin-based endocytotic pathway. For example, potential derivatives (e.g., candidate compounds) for this class of compounds consist of the flavone backbone and up to 5 substitutents (FIG. 1). FIG. 1 shows a flavinoid structure. For EMD21388, $R_1$ and $R_3$ are Br; $R_2$ and $R_5$ are —OH, and $R_4$ is —$CH_3$. Combinatorial chemists can modify this backbone to achieve desired properties. Some candidate compound flavone-derived structures based on R-group substitutions are indicated in FIG. 1.

Figure 2:
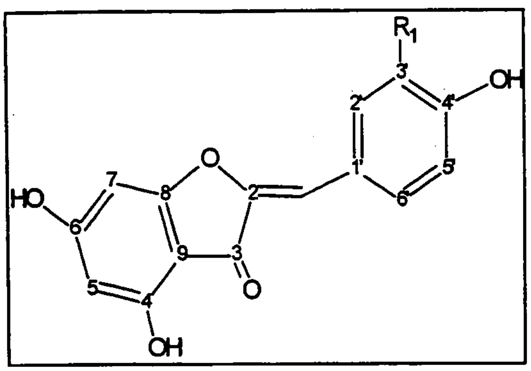
FIG. 2 is a schematic representation of the general structure of aurones.

Aurones are a class of flavones that are candidate compounds (Auf'mkolk et al., 1986, J. Biol. Chem. 261:11623-11630; Auf'mkolk et al., 1986, Biochem. Pharmacol. 35:2221-2227; Auf'mkolk et al., 1984, Hormone Metabol. Res. 16:188-192; Cody et al., 1986, Prog. Clin. Biol. Res. 213:373-382; Koehrle et al., 1986, J. Biol. Chem. 261:11613-11622; Koehrle et al., 1986, Prog. Clin. Biol. Res. 213:359-371) because they may function by inhibiting the deiodination of T4 by type I iodothyronine 5'-deiodinase. FIG. 2 shows the basic structure for aurones. For certain aurones, it has been shown that if R1 (FIG. 2) is either a halide (e.g., I), —OH, or —H, enzyme inhibition is favored. If the —OH is eliminated on C4, inhibition is weakened. Similarly if the 4' —OH is further substituted the molecule is a poor inhibitor.

Figure 3:
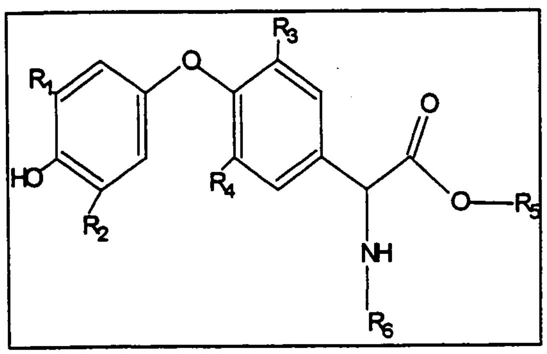
FIG. 3 is a schematic representation of the structure of iodothyronine.

A third class of potential candidate compounds that bind to ΔTRα1 or ΔTRα2 are analogs of thyroid hormone. FIG. 3 depicts the basic strucure for these compounds. lodothyronine is the parent compound. Based on the effects of alanine side chain modifications that either enhance or diminish the ability of T4 or N-blocked T4 molecules to inactivate D2, the following criteria can be used to guide selection of test compounds for use in the invention:

1. Net negative charge on the alanine side chain impairs ligand binding to ΔTRα2.
2. Charge masking or elimination of the carboxyl group of the alanine side chain enhances ligand binding to ΔTRα2.
3. Elimination of one inner-ring iodine (3,5 positions) has no effect on ligand binding to ΔTRα2. Elimination of two inner ring iodine may have no effect on ligand binding.
4. Substitution of other bulky substitutions at the (3', 5' positions) does not generally affected binding to ΔTRα2.

T4 is the compound illustrated by FIG. 3 when $R_1$, $R_2$, $R_3$, and $R_4$ are I, and $R_5$ and $R_6$ are protons. T3 exchanges —H for —I at $R_2$ (or $R_1$), rT3 exchanges a —H for —I at $R_3$ (or $R_4$); 3', 5'-T2 exchanges —H for —I at both $R_3$ and $R_4$. Substitutions at $R_6$ decrease the ability of the iodothyronine to cause D2 inactivation (i.e., bind to ΔTRα2) if $R_5$ is a proton. However, if $R_6$ is substituted, elimination of charge by masking at $R_5$ will enhance the ability of the thyroid hormone analog to inactivate D2 (bind to ΔTRα2; Safran et al., 1993, J. Biol. Chem. 268: 14224-14229). All of these modified thyroid hormones have little, if any, thyromimetic effect in the nucleus; they are generally thought to be metabolically inactive.

Figure 4:
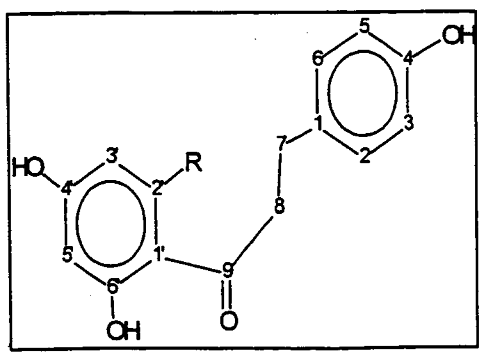
FIG. 4 is a schematic representation of the general structure of phloretin.

Another flavone, phloretin, a 7,8-dihydrochaleone from plants, is a potent inhibitor of deiodination (Auf'mkolk et al., 1986, J. boil. Chem. 261:11623-11630; Auf'mkolk et al., 1986, Biochem. Pharmacol. 35:2221-2227; Auf'mkolk et al., 1984, Hormone Metab. Res. 16:188-192; Cody et al., 1986, Prog. Clin. Biol. Res. 213:373-382; Koehrle et al., 1986, J. Biol. Chem. 261: 11613-111622; Koehrle et al., 1986, Prog. Clin. Biol. Res. 213:359-371). Therefore phloretin and phloretin analogs are possible ligands for ΔTRα2 or ΔTRα1 and can be candidate compounds. The structure of this class of molecules is shown in FIG. 4. In phloretin, R is a —OH.

Cell Types Useful for Assays

The cells useful in the screening assays of the invention are generally from an animal. In most cases the cell will be from a mammal, e.g., a mouse or rat cell. Human cells, either primary, secondary, or cultured cells can also be used. Astrocytes are especially useful for the assays. Methods of culturing astrocytes are known in the art (e.g., Leonard, 1988, Biochem. Biophys. Res. Comm. 151:1164-1172), including methods for preparing and culturing human astrocytes. Other cell types that are useful in the invention include neurons, mixed fetal rat brain cells, neuronal progenitor cells, embryonic stem cells, PC12 cells, C6 astrocytoma cells, and bone marrow stem cells.

This invention further pertains to novel agents identified by the above-described screening assays and uses thereof for treatments as described herein.

Animal Models

Compounds identified as candidate compounds for therapeutic uses related to treating a disorder involving a ΔTRα1 or a ΔTRα2 protein can be tested in animal models of such disorders. For example, the learned helplessness model in rats can be used as a model for certain psychiatric disorders (e.g., Lucki, 1997. Behav. Pharmacol. 8: 523-532; Porsolt, 1979, Biomed. 30:139-140; Porsolt, 2000, Rev. Neurosci. 11:53-58).

Transgenic Animals

The invention encompasses the engineering of cells that can be used to produce nonhuman transgenic animals. For example, in one embodiment, such a cell is a fertilized oocyte or an embryonic stem cell that has been genetically engineered to lack competent promoters in intron 7 of a mouse thyroid hormone receptor gene. Another example of such a cell is one in which exon 10 of a mouse thyroid hormone receptor gene has been deleted or altered. Such engineered cells can be used to create non-human transgenic animals in which the modifications of the invention (i.e., modifications that alter the expression of a thyroid hormone receptor) have been introduced into their genome or homologously recombinant animals in which the endogenous thyroid hormone receptor gene has been altered. Such animals are useful for studying the function and/or activity of a ΔTRα1 or a ΔTRα2 protein, and for identifying and/or evaluating modulators of ΔTRα1 or ΔTRα2 activity.

A transgenic animal of the invention can be created by introducing nucleic acid containing the desired alteration in a thyroid hormone receptor gene into the male pronuclei of a fertilized oocyte, e.g., by microinjection or retroviral infection, and allowing the oocyte to develop in a pseudopregnant female foster animal. Intronic sequences and polyadenylation signals can also be included in the transgene to increase the efficiency of expression of the transgene. If desired, a tissue-specific regulatory sequence(s) can be operably linked to the transgene to direct expression of the altered gene to particular cells. Methods for generating transgenic animals via embryo manipulation and microinjection, particularly animals such as mice, are known in the art and are described, for example, in U.S. Pat. Nos. 4,736,866 and 4,870,009, 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. Additional methods of identifying such animals are described below in Example 4. A transgenic founder animal can then be used to breed additional animals carrying the transgene. Moreover, transgenic animals carrying the transgene can further be bred to other transgenic animals carrying other transgenes.

To create a homologously recombinant animal, a vector is prepared which contains at least a portion of a gene encoding a thyroid hormone receptor gene into which a deletion, addition or substitution has been introduced to thereby alter, e.g., functionally disrupt, the gene. In one embodiment, the vector is designed such that, upon homologous recombination, the endogenous gene is functionally disrupted (i.e., no longer encodes a functional protein; also referred to as a "knock out" vector), e.g., by altering the promoter of intron 7 of a mouse thyroid hormone receptor gene. Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992, Cell 69:915).

The selected cells are then injected into a blastocyst of an animal (e.g., a mouse) to form aggregation chimeras (see, e.g., Bradley in Teratocarcinomas and Embryonic Stem Cells: A Practical Approach, Robertson, ed., (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829 and in PCT Publication Nos. WO 90/11354, WO 91/01140, WO 92/0968, and WO 93/04169.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of Saccharomyces cerevisiae (O'Gorman et al., 1991, Science 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication No's. WO 97/07668 and WO 97/07669.

The invention also includes populations of cells derived from transgenic animals of the invention.

These transgenic animals are useful for examining the role of ΔTRα polypeptides or proteins in whole animal physiology since the physiology and phenotypes of transgenic animals lacking a ΔTRα will reveal other systems besides nervous system where these molecules may have a function. Such animals can also be used to study the role of ΔTRαs in the nervous system. Transgenic animals of the invention are also useful, e.g., for studying non-TR-related effects of candidate compounds. This can be done by administering a candidate compound to a transgenic animal that does not express a ΔTRα. Effects of the candidate compound on the animal are examined. Adverse effects on the transgenic animal may be predictive of adverse effects that could occur should the candidate compound be used as a treatment for one of the disorders described herein. Candidate compounds with adverse effects are less likely to be useful as drugs to treat a disorder. The method of testing candidate compounds on transgenic mice lacking a ΔTRα can thus be used as a step in selecting those candidate compounds which are the best candidates to use for clinical studies in, e.g., humans.

Methods of Treatment

The present invention provides for both prophylactic and therapeutic methods of treating a subject at risk of, or susceptible to, a disorder, or having a disorder, associated with expression or activity of a ΔTRα1 or a ΔTRα2. Such expression or activity can be aberrant or normal. For example, disorders characterized by aberrant expression or activity of a ΔTRα1 or a ΔTRα2 protein or in which an alteration of normal expression or activity include certain psychiatric or neurologic disorders of the nervous system, e.g., mood disorders. Disorders that can be treated using the molecules of the invention (e.g., modulators of ΔTRα1 or ΔTRα2 expression or activity) include bipolar disorder, major depression, attention deficit disorder, attention deficit hyperactivity disorder, and obsessive-compulsive disorder, as well as other disorders described herein.

In some cases, the therapeutic molecules identified using the methods described herein may be used as prophylactic treatments of those considered at-risk for a disorder that is treated using the therapeutic molecule.

Effective Dose

Toxicity and therapeutic efficacy of the compounds of the invention can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the methods of the invention, the therapeutically effective dose can be estimated initially from cell culture assays. A dose can also be calculated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma can be measured, for example, by high performance liquid chromatography. Dosages are from about 1 μg to 500 mg per day. Typically, dosages are from about 5 μg-500 μg per day. Because circulating plasma levels of a compound can differ substantially from levels circulating in the cerebrospinal fluid (CSF), in some cases it may be preferable to measure CSF levels of the compound.

Formulations and Use

Pharmaceutical compositions for use in accordance with the present invention can be formulated in a conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use.

Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectally administered compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences."

Uses

The screening methods and transgenic animals of the present invention are useful for identifying compounds that can affect endocytosis and vesicle transport. The invention is especially useful for identifying compounds that affect synaptic vesicle transport and as such can be used for treating disorders involving the nervous system, e.g., antidepressants. Without committing to any particular theory, the data upon which the invention is based suggest that thyroid hormone can target vesicle pools. Neurotransmitters are released from axons and many are recycled back into the cell through re-uptake mechanisms involving vesicle pools. There are differences between vesicles within the pools, e.g., vesicles located near the axonal hillock tend to contain greater concentrations of neurotransmitters than do those located near the axon terminal. Because the data upon which the present invention is based suggest that thyroid hormone is likely to cause vesicles to move further from the nerve terminus, the vesicles are likely to contain greater concentrations of neurotransmitter, causing less depletion of neurotransmitters. Some anti-depressants act by raising the amount of a specific neurotransmitter (e.g., serotonin) in the synaptic cleft. The modulators of the present invention may therefore act to promote more efficient recycling of neurotransmitters between the cleft and the cell. Thus, for example, lower concentrations of anti-depressants may be required to achieve a therapeutic effect, and/or there may be improved therapeutic effect of an anti-depressant delivered at standard dosages.

EXAMPLES

The invention will be further described in the following examples, which do not limit the scope of the invention described in the claims.

Example 1

Materials and General Methods

Materials

T4 (thyroxine), Triton X-100®, ATP, bt2cAMP, hydrocortisone, colchicine, bovine serum albumin, and rabbit anti-actin IgG were obtained from Sigma (St. Louis, Mo.). Dulbecco's modified Eagle's medium, antibiotics, Hank's solution, and trypsin were purchased from GIBCO (Grand Island, N.Y.). Acrylamide was purchased from National Diagnostics (Atlanta, Ga.). TEMED and ammonium persulfate was purchased from Bio-Rad (Richmond, Calif.). Hybond ECL nitrocellulose was obtained from Amersham (Arlington Heights, Ill.); horseradish peroxidase conjugated goat, anti-rabbit IgG was obtained from Promega (Madison, Wis.); rabbit anti-GFP IgG was from Clontech (Palo Alto, Calif.). The Lumiglo® chemiluminescent detection system was obtained from Kirkegaard and Perry (Gathersburg, Md.). BrAc[$^{125}$ I]T4 was synthesized as described in Köhrle et al. (1990, J. Biol. Chem. 265:6155-6163). Restriction endonucleases and DNA modifying enzymes were purchased from New England Biolabs (Beverly, Mass.).

Culture Preparation

Astrocytes were prepared from one day old neonatal rats as described in Leonard (1988, Biochem. Biophys. Res. Comm. 151:1164-1172) and cultured in Growth medium composed of Dulbecco's modified Eagle's medium supplemented with 10% supplemented bovine calf serum, 50 units/ml penicillin, 90 units/ml streptomycin. Cells were grown to confluence in 75 $cm^2$ culture flasks in a humidified atmosphere of 5% $CO_2$ and 95% air at 37° C., and used at passages 1-3.

Myosin V

The Genbank number of the myosin V (also referred to as myosin 5a; myo 5a) sequence used for the experiments described below is X57377.

Antibody Preparation

Synthetic peptides corresponding to the last 22 amino acids C-terminus of myosin V (NH2-YSLALETIQIPASLGLGFIARV—COOH; SEQ ID NO: 1) were synthesized. An N-terminal tyrosine was added to facilitate diaminobenzidine coupling to KLH (Keyhole Limpet hemocyanin) and for radioiodination. Peptide-KLH conjugate (750 μg KLH conjugate/500 μl) was mixed with an equal volume of Complete Freund's adjuvant and injected intradermally at 20 sites on the backs of 2.2 kg female New Zealand White Rabbits.

Antibodies were also raised against an internal myosin V domain corresponding to the last IQ domain and the coiled-coil region (residues 892 to 1040, myosin $V^{cc}$). PCR amplified myosin V cDNA was prepared using site specific, 20-mer oligonucleotides; the approximately 500 bp fragment was cloned into the EcoRV site of the pThioHis B prokaryotic expression vector (Invitrogen, San Diego, Calif.) and the fusion protein was synthesized in IPTG induced *E. coli*. The myosin $V^{cc}$ fusion protein was purified on Ni-Sepharose (Clontech) from cell lysates according to manufacturer's instructions. Approximately 75 μg of myosin $V^{cc}$ was diluted 1:1 with Freund's complete adjuvant and used to immunize rabbits as described above.

The specificities of the rabbit anti-myosin V antisera were documented by immunoblot analysis. Brain homogenates were prepared from phenotypically normal, heterozygous (myosin $V^{+/-}$) and myosin V-deficient, homozygous dilute mouse (myosin $V^{-/-}$). Both antibodies recognized a 190 kDa protein in the brain homogenates containing myosin V (heterozygotes) but showed no immunoreactive band in the homogenates of dilute mouse brain that lacks myosin V.

Immunoblotting

Total cell protein was measured by the Bradford dye binding assay (Sigma, St. Louis, Mo.). To prepare samples, 20-50 μg of cellular protein was reduced, denatured and separated by SDS-PAGE (Laemmli, 1970, Nature 227: 680-685). Resolved proteins were transferred to Hybond membranes by electrotransfer using a Semi-Dry transfer apparatus (200 mA for 1 hour). The membrane was blocked in TRIS-buffered saline (pH 7.5) containing, 0.1% Tween 20 (v/v) and 5% powdered milk (w/v; TTBS/5% milk). Immunoblots were then probed with primary antibodies (1:500 for anti-Myosin V antisera; 2 μg/ml for anti-GFP (Green Fluorescent Protein IgG) for 16 hours at 4° C. After washing, immune complexes were detected with HRP (horseradish peroxidase)-conjugated, goat, anti rabbit IgG (1:2000 final dilution) and the specific complexes visualized by chemiluminescence and Kodak XOMAT® AR5 radiographic film.

Construction of Replication-deficient, Myosin V Viral Vectors

The 3280 base pair fragment containing the coding sequence of the globular myosin V tail cDNA (myosin $V^{tail}$) were excised from clone D64 (Huang et al., 1998, Genetics 148:1963-1972) with SspI and Eco47III, and ligated into the EcoRV site of the AdpREC shuttle vector (T. Kowalik, UMMC). The shuttle construct was linearized with EcoRI and cotransfected with Xba-ClaI linearized Ad5-gal into HEK 293 cells (ATCC No. CRC-1573) using lipofectin according to manufacturer's instructions. Replication-deficient Ad5-myoV containing virus particles were purified from the HEK293 cell lysates by cesium chloride gradient centrifugation. Other suitable vectors may be used.

Expression of myosin V from Ad5-myoV infected cells was confirmed by Western blot analysis. The Ad5-$p29^{GFP}$ virus particles were generated as described in Visser et al. (1982, Proc. Nat. Acad. Sci. USA 79:5080-5084).

Immunocytochemistry

Astrocytes were seeded onto to poly-d-lysine (10 μg/ml) coated coverslips. Myosin V distribution was determined in bt2cAMP-stimulated astrocytes treated or untreated with T4. Cells were fixed with 4% paraformaldehyde and permeabilized with 0.1% Triton x-100®.

To visualize myosin V, anti-myosin V IgG (C-terminus) was used at a final dilution of 1:500. The immune complexes were visualized using a Texas Red-conjugated donkey, anti-rabbit IgG (dil 1:50). Twenty to 50 random fields were examined by fluorescence microscopy.

Example 2

Specificity of ΔTRα1 and ΔTRα2 Binding

The properties of thyroid hormone binding to non-nuclear components of the cell were examined using ΔTRα2 (T4 Inactivating Protein; TIP)-containing, nuclei-free extracts of cultured rat astrocytes. Reverse T3 (rT3) was used as the ligand because of its potent biological effect on D2 (type II 5'deiodinase) endocytosis and its low avidity for any contaminating nuclear thyroid hormone receptors. Both rT3 and T4 specifically displace rT3 with $K_d$'s of approximately 0.3-0.5 nM. Subcellular localization of the specific $rT_3$ binding sites revealed that ΔTRα2 was most abundant in subcellular fractions containing cellular membranes and the cytoskeleton.

ΔTRα1 and ΔTRα2 polypeptides were synthesized by cell-free translation of appropriate segments of the rat ΔTRα1 and ΔTRα2 cDNA using the coupled transcription-translation kit from Promega® ($T_NT$) according to the manufacturer's instructions. Synthesis of the appropriate sized translation product(s) was confirmed by SDS-PAGE. The thyroid hormone displacement curves for $rT_3$ binding to ΔTRα1 and ΔTRα2 demonstrated that both ΔTRα1 and ΔTRα2 specifically bound from 3 to 5% of the total [$^{125}$I] rT3. Also, both T4 and rT3 specifically displaced [$^{125}$I]rT3 with $K_d$'s of about 0.3 to 1 nM. These data are identical to those for native ΔTRα2 found in astrocyte lysates. T3 did not displace [$^{125}$I]rT3 from either thyroid hormone receptor at concentrations up to 100 nM, consistent with the failure of T3 to initiate actin-based endocytosis or bind to TIP in astrocyte lysate. Control studies done with cell-free translated β-galactosidase showed no specific rT3 binding.

These data indicate that ΔTRα1 and ΔTRα2 polypeptides can act as high affinity thyroid hormone binding proteins ($K_d$~0.4 nM) that favors fully outer ring substituted iodothyronines. Such a protein is present in rat astrocytes. These data also show that the thyroid hormone specificity of ΔTRα1 and ΔTRα2 is different from that of the nuclear thyroid hormone receptors. Both ΔTRα1 and ΔTRα2 show similar thyroid hormone binding preferences and affinities.

Example 3

Identification of ΔTRα's in Myosin V-Enriched Synaptic Vesicles from Rat Brain

To further examine the role in the brain of the truncated thyroid hormone receptors (ΔTRα's), myosin V-enriched synaptic vesicles were prepared from rat cerebral cortex and cerebellum using the method of Evans et al. (1998, J. Cell Sci. 111: 2055-2066), and characterized by immunoblot for the presence of the expected synaptic vesicle proteins and for ΔTRα1 and ΔTRα2.

Myosin V comprises approximately 0.3% of total protein in brain. Cultured astrocytes were examined in untreated (control) and T4-treated cells for the presence and distribution of myosin V using Western Blot analysis and immunocytochemistry. Cultured astrocytes were treated overnight with 10 μM retinoic acid ±10 nM T4. Cells were collected by scraping and lysed by two freeze-thaw cycles. Triton X-100® supernatants and pellets were prepared as described herein and equivalent volumes of resuspended Triton pellet and Triton supernatant, and whole cell lysate were separated on 5-20% linear gradient SDS-PAGE gels and transferred to nitrocellulose. Immunoblot analysis was then performed.

More than 80% of the 190 kDa, immunoreactive myosin V was found in the Triton-insoluble pellets prepared from retinoid-treated astrocytes in the absence or presence of T4. Pre-incubation of the anti-myosin V antibody with excess blocking peptide (10 μg/ml) completely eliminated the 190 kDa immunoreactive band, indicating that the myosin V present in astrocytes is predominantly associated with the F-actin cytoskeleton. No differences in total actin content were observed between the Triton supernatant and Triton pellet from retinoid-treated astrocytes that were grown in absence and presence of thyroid hormone. More than 95% of the immunoreactive actin was found in the Triton-insoluble pellet in both thyroid hormone deficient and T4-treated cells. These data demonstrate that retinoid-treated, thyroid hormone deficient astrocytes contain a fully polymerized actin cytoskeleton and that myosin V is constitutively bound to F-actin.

Using immunocytochemistry to localize myosin V in astrocytes treated in the absence and presence of 10 nM T4, it was observed that immunoreactive myosin V was found in the perinuclear space, and diffusely distributed throughout the cell in the absence and in the presence T4. These data indicate that astrocytes express abundant myosin V and that quantity of myosin V in the cell is not dependent on thyroid hormone. Thus, it is not expected that candidate compounds of the invention will affect the amount of myosin V present in a cell.

Immunocytochemical methods were used to examine proteins associated with myosin V-enriched synaptic vesicles isolated from rat cerebellum and cerebral cortex. The synaptic vesicles were found to contain abundant immunoreactive myosin V, actin, and Rab3. Neither synaptic vesicle pool showed any TRα1-derived protein(s) using antibodies that recognize the unique C-terminus of these polypeptides. By contrast, both synaptic vesicle preparations showed a TRα2 signal with the expected Mr of ΔTRα2.

These data show that an immunoreactive ~26 kDa polypeptide (ΔTRα2) is present in synaptic vesicles enriched for myosin V and indicate that ΔTRα2 and its ligands play a role in synaptic vesicle function.

Example 4

Cellular and Subcellular Localization of the TRα-derived Polypeptides in Mixed Brain Cell Cultures and in Rat Astrocytes The subcellular distribution of immunoreactive thyroid hormone receptor-derived proteins in primary brain cell cultures and in cultured astrocytes was examined. Primary brain cell cultures were fixed with 0.4% paraformaldehyde, permeabilized with Triton X-100®, and stained for TRα-derived proteins using specific antisera directed against the unique C-termini of TRα1 and TRα2 proteins, and visualized by staining with a secondary tagged antibody. Consistent with previous observations (Kolodny et al., 1985, Endocrinol. 117: 1848-1857), immunoreactive TRα1 proteins were found in the nuclei of astrocytes and neuronal cells. However, TRα2-derived proteins were not localized to the nucleus in either astrocytes or neurons, but appeared as donut shaped structures located throughout the astrocyte or as discreet punctate signals along neuronal fibers. This latter pattern is diagnostic for synapses in neuronal cultures (Wong et al., 1999, Neurosci. 89:221-233), and is consistent with the presence of ΔTRα2-derived protein in nerve terminals.

The subcellular distribution of immunoreactive TRα2-derived proteins in cultured astrocytes was influenced by the presence of either T4 or rT3. In these experiments astrocytes were grown in serum-free medium, treated for 20 minutes with either rT4 or rT3, and fixed, permeabilized, and stained as described above. In the absence of thyroid hormone, TRα2-derived proteins were distributed throughout the cell and along the cell periphery, but were not concentrated in the cell nucleus. Addition of either rT3 or T4 in 0.1% bovine serum albumin as a carrier led to the coalescence of the TRα2-derived proteins around the perinuclear space of the astrocyte, a distribution similar to that shown for the TH-dependent endocytosis of p29 (D2) vesicles. Thus, it appears that TRα2-derived protein(s) are found in the nerve terminals of neurons grown in vitro and these immunoreactive TRα2-derived polypeptides show thyroid hormone-dependent internalization and relocalization in cultured astrocytes.

Example 5

Characterization of the TH-dependent Binding of Vesicle Docking Proteins and ΔTRα2 to F-actin Fibers through the C-terminus of Myosin V Myosin V is a 190 kDa protein that is widely distributed in the brain (Cheney et al, 1993, Cell 75, 13-23; Wagner et al, 1992, J. Cell Biol. 119: 163-170). p29 (D2) vesicle pull-down (immunoprecipitation) assays or F-actin isolation (supra) revealed that Rab3, synaptophysin, and synaptotagmin were constitutive elements of p29 vesicles, thus demonstrating a link between p29 vesicles and synaptic vesicles. Both myosin V and ΔTRα2 showed thyroid hormone-dependent association with p29 vesicles. In contrast, when the proteins bound to the F-actin cytoskeleton were analyzed, both myosin V and ΔTRα2 appeared to be constitutively bound to F-actin, while the synaptic vesicle proteins showed thyroid hormone-dependent association with the microfilaments. These data add additional support to the discovery that thyroid hormone directly influences synaptic vesicle transport.

Characterization of the Interaction(s) between the Myosin V Tail and p29 Vesicles.

Since the approximately 80 kDa globular tail of myosin V specifically binds to synaptic vesicles (Prekeris and Terrian, 1997, J. Cell Biol 137:1589-1601), myosin V mutants lacking the actin-binding head would be expected to compete with the native, F-actin bound myosin V for the p29 vesicles, thereby blocking the thyroid hormone-dependent binding of p29 vesicles to F-actin. Initial studies used the entire C-terminus of myosin V synthesized in vitro from a 4.2 kb fragment (nt2911-nt7087) of the myosin V cDNA (Δ myosin $V^{tail}$) using a coupled transcription and translation system (TNT®, Promega). Cell-free synthesis of the appropriate myosin V fragment was confirmed by immunoblot and an 88 kDa band was detected using anti-myosin V antibodies directed against the C-terminal 22 amino acids. Increasing volumes (5 or 10 μl) of Δ myosin $V^{tail}$ or a comparable volume of control reticulocyte lysate were added to the in vitro actin binding assay (see infra) and pre-incubated for 20 minutes at 37° C. Actin binding of the p29 vesicles was then initiated by addition of 10 nM T4, and the Triton-insoluble (F-actin bound) pellet was separated from the Triton-soluble (vesicle) fraction.

Addition of 5 μl of Δ myosin $V^{tail}$ blocked about 50% of the T4-dependent binding of p29 vesicles to F-actin, while the addition of 10 μl of Δ myosin $V^{tail}$ blocked more than 95% of the p29 binding. In control binding assays, addition of up to 10 μl of the reticulocyte lysate failed to affect the T4-dependent p29 vesicle binding to F-actin. These data indicate that the loss of the actin-binding head of myosin V generates a Triton-soluble myosin V mutant that will compete with the wild type motor and block the T4-dependent binding of p29 vesicles to the actin cytoskeleton and so demonstrates the involvement of myosin V in the T4-dependent binding. Thus, ΔTRα2 interacts with the C-terminal region of myosin V, based on the ability of a headless myosin V deletion mutant lacking the actin binding head, the neck and coiled-coil domains to bind ΔTRα2 and shift the distribution of this effector molecule to the cytoplasm.

Monitoring myosin V binding can therefore be used as an assay for T4 analogs involved in T4-dependent binding of p29 vesicles to the actin cytoskeleton.

Use of $p29^{GFP}$ Labeled Vesicles to Analyze Myosin V Function in Rat Astrocytes To define the specific region(s) of the myosin V tail that interact with the p29 vesicle, a series of deletion mutations were created based on the dominant negative effect of exogenous myosin V tail on p29 vesicle binding. Competition analysis of the myosin V deletion mutations on T4-dependent binding of p29 vesicles to F-actin was performed using a modified in vitro assay in which a GFP-tagged p29 fusion protein ($p29^{GFP}$) replaced the radioaffinity labeled native p29 (Farwell et al., 1990, J. Biol. Chem. 265:18546-18553; Farwell et al., 1993, J. Biol. Chem. 268:5055-5062). This allowed direct evaluation of the binding of fluorescent vesicles to F-actin without affinity radiolabeling of the p29 and subsequent SDS-PAGE analysis.

To confirm that the $p29^{GFP}$-labeled vesicles showed the same hormone dependent attachment to the actin cytoskeleton as observed for the radioaffinity labeled p29 (Farwell et al., 1990, supra; Farwell et al., 1993, supra) exogenous $p29^{GFP}$ was introduced into the astrocytes used to prepare the V-lysate by infection with replication deficient Ad5-$p29^{GFP}$ virus particles. Equal volumes of F-lysate and V-lysate containing $p29^{GFP}$-labeled vesicles were incubated with increasing concentrations of T4, rT3, or T3 (0-100 nM) for 20 minutes at 37° C., and Triton-soluble and Triton-insoluble fractions were separated by microfuge centrifugation. Specific fluorescence at 510 nm (excitation, 488 nm) was then determined in the resuspended Triton-insoluble pellets. Dose-response studies demonstrated that both T4 and rT3 showed concentration dependent increases in the quantity of $p29^{GFP}$ bound to the F-actin with EC50's of about 0.5 nM, identical to those reported previously (Farwell and Leonard, 1992, Endocrinol., 131:721-728). As expected, T3 did not increase $p29^{GFP}$ vesicle binding to F-actin, except for a modest 10-20% observed at 100 nM T3, the highest concentration of hormone used. These data illustrate that the modified in vitro binding assay faithfully reproduces the results obtained with affinity radiolabeled p29.

To determine if the myosin V tail could be captured by the $p29^{GFP}$ vesicle, an exogenous myosin $V^{tail}$ was introduced into astrocytes constitutively expressing $p29^{GFP}$ by infection with Ad5-ΔMyo $V^{tail}$ virus particles and examined the effects of T4 on the binding of the myosin $V^{tail}$ to immunopurified $p29^{GFP}$ vesicles. Astrocytes expressing $p_{29}{}^{GFP}$ were grown in serum-free media and treated for 16 hours with 1 mM $bt_2cAMP$ and 100 nM hydrocortisone. A separate pool of astrocytes was treated in serum-free media supplemented with 10 μM retinoic acid. Cells were collected by scraping, and lysed by two freeze-thaw cycles. 100 μg aliquots of $p_{29}{}^{GFP}$ V-lysate and F-lysate were incubated, in triplicate, for 20 minutes with increasing concentrations of T4, T3, or rT3. Triton-soluble (vesicle) and Triton-insoluble (F-actin) fractions were separated by microflige centrifugation. Triton pellets were resuspended in 300 μl of PBS and fluorescence at 510 nm (excitation 488 nm) determined and relative fluorescence was reported as arbitrary units. Cells were treated with 10 nM T4 for twenty minutes and a Triton-soluble supernatant was prepared. Vesicles containing the $p29^{GFP}$ were immunoprecipitated by anti-GFP IgG (2 μg/ml) and protein in the immunoprecipitates were resolved by SDS-PAGE. Immunoblot analysis of vesicle-associated myosin V was performed using the anti-myosin V antibody directed against the C-terminus.

In control cells expressing the $p29^{GFP}$ alone, no myosin V immunoreactive protein was detected in the purified vesicle pool since the native myosin V is constitutively bound to the Triton-insoluble F-actin (see above). In contrast, expression of the truncated (Δ) myosin V in $p_{29}{}^{GFP}$ expressing cells showed a T4-dependent association between myosin V and $p29^{GFP}$ vesicle, as judged by the appearance of an 88 kDa immunoreactive band. Since there was no interaction between the myosin $V^{tail}$ and p29 vesicle in the absence of T4, these data show that the direct interaction between the p29 vesicle and myosin V is hormonally regulated.

Figure 5:
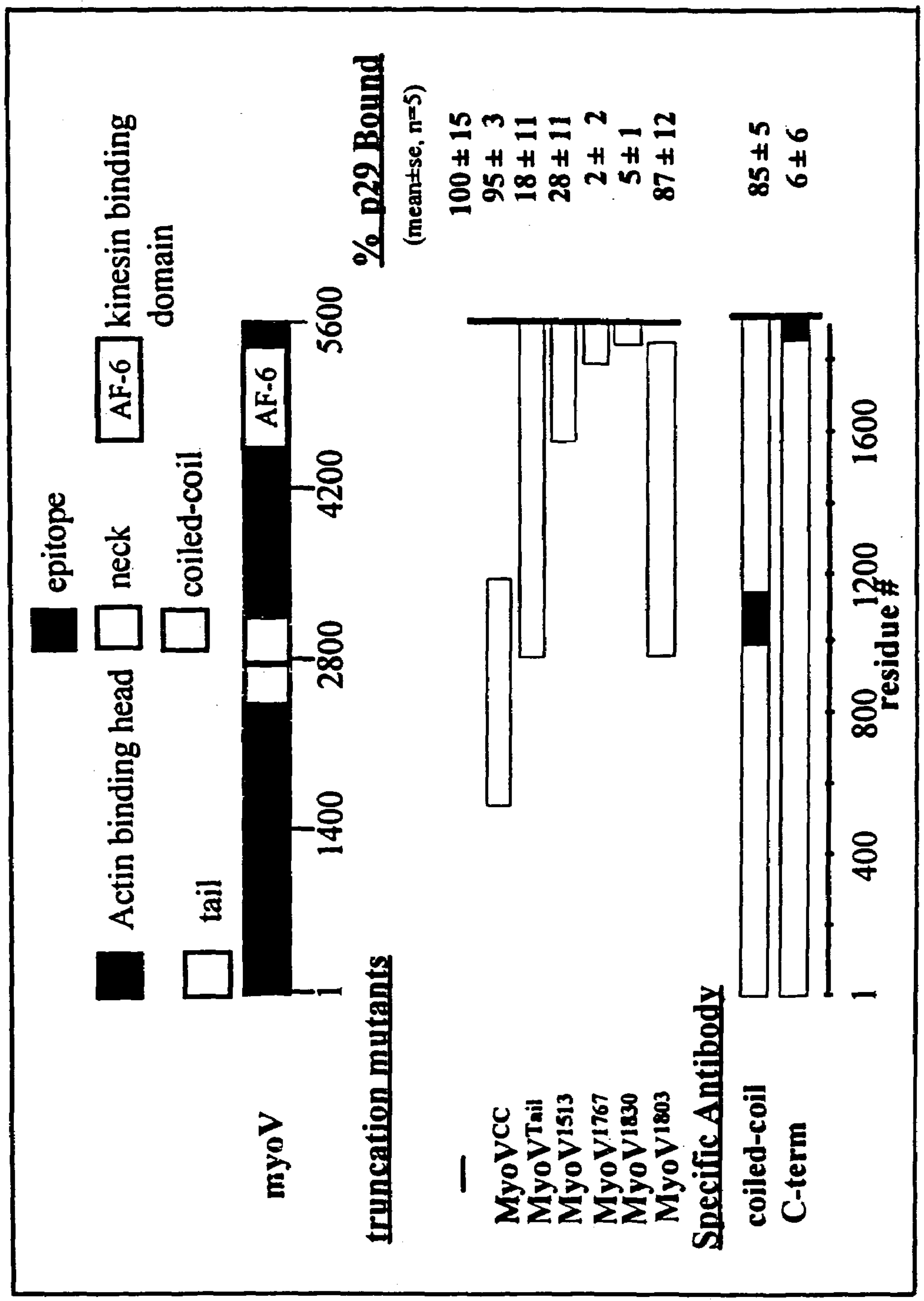
FIG. 5 is a diagram of myosin V truncation mutants and indicates the percentage of p29 binding to myosin V competed out by each mutant peptide.

Myosin V truncation mutants were used to further define the role of myosin V in mediating the binding of $p_{29}{}^{GFP}$ to the F-actin cytoskeleton. FIG. 5 shows a schematic diagram of the myosin $V^{tail}$ deletion mutations studied and the results of competition experiments investigating the amount of p29 binding to myosin V in the presence of each of the truncation mutants.

To perform the competition experiments, the deletion mutants were synthesized by cell-free translation and the synthesis of the correct myosin V polypeptides was confirmed by Western blot analysis. The quantity of each mutant protein synthesized was determined by [$^{35}$ S]-methionine incorporation. Astrocytes expressing $p_{29}{}^{GFP}$ were grown in serum-free media and treated for 16 hours with 1 nM bt2cAMP and 100 nM hydrocortisone. $p_{29}{}^{GFP}$ V-lysate and F-lysate were prepared as described herein. 100 μg aliquots of $p_{29}{}^{GFP}$ V-lysate and F-lysate were pre-incubated, in triplicate, for 20 minutes at 37° C. in the presence of individual Δ myosin V mutant proteins (~2-3 pmol polypeptide/50 μl mixture) were added to the actin-binding assay and pre-incubated for 20 minutes at 37° C. T4 (10 nM) was then added, the mixtures incubated for 20 minutes at 37° C., and F-actin bound, fluorescent $p_{29}^{GFP}$ vesicles were then isolated in the Triton-insoluble pellet.

Addition of the A myosin V middle protein, corresponding to amino acids 504-1307, did not compete with native myosin V for the T4-dependent binding of p29 to F-actin. Addition of the entire myosin $V^{tail}$ (residues 953 to 1852) decreased p29 binding to F-actin by more than 75% ($p<0.01$). Addition of progressively shorter myosin $V^{tail}$ deletion mutants, Δ myosin $^{1513}$ (residues 1513-1852), Δ myosin $^{1767}$ (residues 1767-1852), and Δ myosin $^{1830}$ (residues 1830-1852), demonstrated that all competed with native myosin V and decreased T4-dependent p29 binding by more than 75%.

Consistent with the idea that the C-terminus of myosin V contains the vesicle binding region, synthesis of a myosin V tail lacking the last 44 residues (residues 953-1803) yielded a truncation mutant that did not compete with native myosin V for T4-dependent p29 vesicle binding. These data demonstrate that the vesicle binding region of myosin V that is responsible for T4-dependent, tethering of the p29 containing vesicles is located in the last 22 amino acids found at the C-terminus of myosin V. These data show that peptides containing at least the last 22 amino acids of the C-terminus of myosin V may be useful in assays of candidate compounds that affect T4-dependent binding to vesicles.

Antibodies Directed Against the C-terminus of Myosin V Block the T4-dependent Binding of p29 Vesicles Antibody inhibition experiments were performed to confirm that ΔTRα2 mediates the TH-dependent binding of the p29 vesicle to actin fiber and to confirm the location of the vesicle-tethering region of myosin V. Two antibodies were used; one directed against the coiled coil domain (residues 892 and 1040), and one directed against the C-terminal 22 amino acids (residues 1830-1852).

Figure 9:
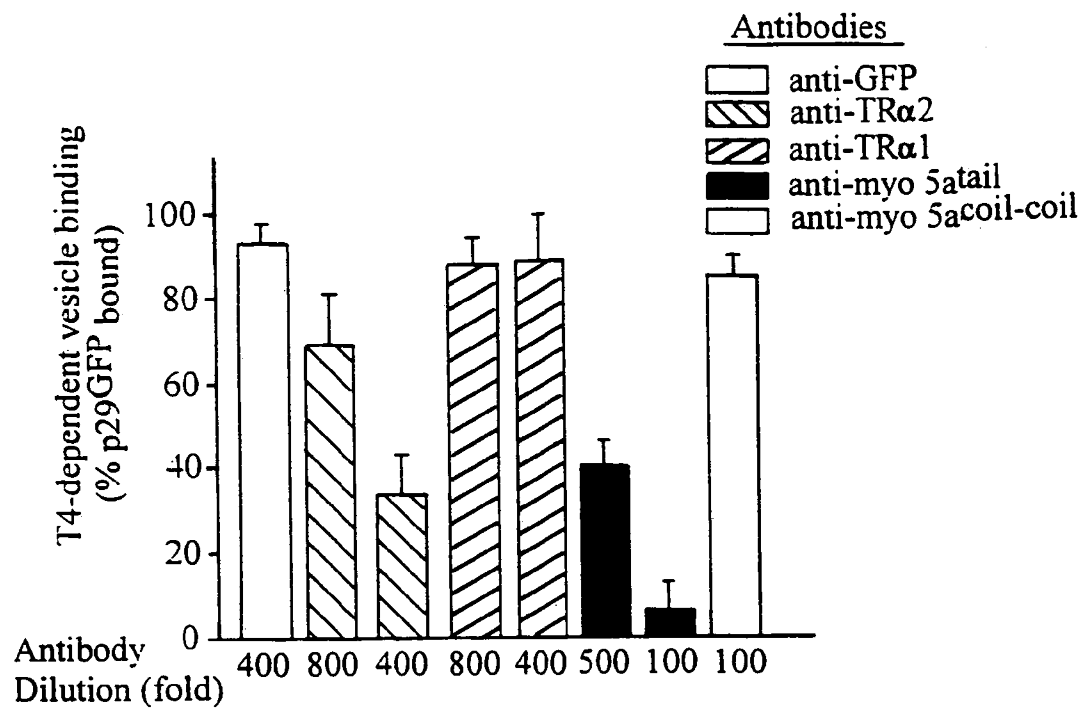
FIG. 9 is a graph illustrating the antibody inhibition of TH-dependent p29 vesicle binding to actin fibers in vitro.

V lysates prepared from astrocytes over-expressing $p29^{GFP}$ were pre-incubated for 30 minutes at room temperature with antisera raised against ΔTRα2, ΔTRα1, the C-terminus of MyoV (encoded by $MyoV^{tail}$, FIG. 5), the coiled-coil region of MyoV (encoded by $MyoV^{coil-coil}$, FIG. 5) and GFP (green fluorescent protein). T4 (10 nM) and actin fiber-containing F-lysate was then added, the mixtures incubated at 37° C. for 20 minutes, and the Triton-insoluble fraction isolated by centrifugation. As shown in FIG. 9, anti-GFP and anti-$MyoV^{coil-coil}$ antibodies had no effect on p29 vesicle binding. Anti-$MyoV^{tail}$ antibody showed concentration dependent inhibition of p29 binding. Anti-TRα1-specific antibodies failed to alter p29 binding to actin fibers, while anti-TRα2 antibodies showed a concentration dependent inhibition of p29 binding similar to that of the anti-$MyoV^{tail}$ antibody.

The data indicate that antibodies directed against the extreme C-terminus of myosin V nearly completely blocked the T4-dependent binding of p29 vesicles, while antibodies directed against the coiled-coil domain generated only a modest 15-20% decrease in p29 vesicle binding. Control rabbit immunoglobulins had no effect of the T4-dependent binding of p29 vesicles to myosin V. These data confirm the assignment of the vesicle-tethering domain to the C-terminus of myosin.

These data indicate that the interaction between the p29 vesicle and F-actin is mediated by thyroid hormone-dependent binding of the vesicle to myosin V, presumably through ΔTRα2. These data support the assertion that thyroid hormone plays a role in mediating actin-based synaptic vesicle endocytosis/transport, specifically through the binding of myosin V to p29 vesicles. p29 is the substrate binding subunit of D2. A decrease in the amount of D2 expression or activity is therefore useful for modulating actin-based endocytosis, e.g., is a useful method of altering neurotransmitter reuptake.

Example 5

Transgenic Mice Lacking ΔTRα1 and ΔTRα2 Binding Activity

The invention also relates to transgenic animals with altered ΔTRα1 and ΔTRα2 expression. The loss of either of these receptors is expected to result in animals with profound defects in neural integration, poor synaptic function, and premature death. These animals are useful for characterizing the role of ΔTRα1 and/or ΔTRα2 in neurogenesis and synapse function, providing information regarding the role of thyroid hormone in the brain, identifying targets for use in drug discovery, and testing candidate compounds for their effects, including effects that are not mediated by ΔTRα1 and ΔTRα2.

General methods of generating such animals are described above: the following provides specific examples of generating such transgenic animals.

Cloning of Exons 7-10

To generate constructs that can be used to generate the transgenic mice described herein, the exons containing the promoters for the ΔTRs were cloned. The hinge region: ligand binding domain of GenBank X07751 (nucleotides 360-1357) was used to screen an SV129 lambda fixII genomic library using random primed $^{32}$P-cDNA probes using methods known in the art (Ausubel et al., eds., 1995, last update April, 2000, Current Protocols in Molecular Biology, John Wiley & Sons, NY). After screening, plaques that hybridized were purified and two clones were selected that contained inserts of 8 kb and 9 kb. Restriction mapping revealed that these two clones span exons 6-9 of the thyroid hormone receptor gene and contained intron 7. Similar methods can be used to isolate genomic sequence encompassing intron 10 from the mouse thyroid hormone receptor gene or from the thyroid hormone receptor genes of other species where cDNA sequences are known.

Elimination of Intron 7 Promoters/transcription Initiating Sequences

Certain transgenic animals of the invention have the promoters and/or transcription initiating sequences of intron 7 (in the mouse or the homologous sequences in other animals) altered or eliminated. One method of eliminating the ΔTRα gene products is to remove the promoter region located in intron 7 of the TRα gene using homologous recombination. Knock-in of a lox P $neo^r$ gene selection cassette into intron 7 of the TRα gene, is followed by recombinant ES cell selection. The $neo^r$ selection cassette is then removed thereby restoring a shortened promoterless intron 7 and the mutant ES cells will be used to generate mice lacking both ΔTRαs but expressing all full-length TRα gene products. Similar methods may be used to alter the intron 7 promoters.

Figure 6:
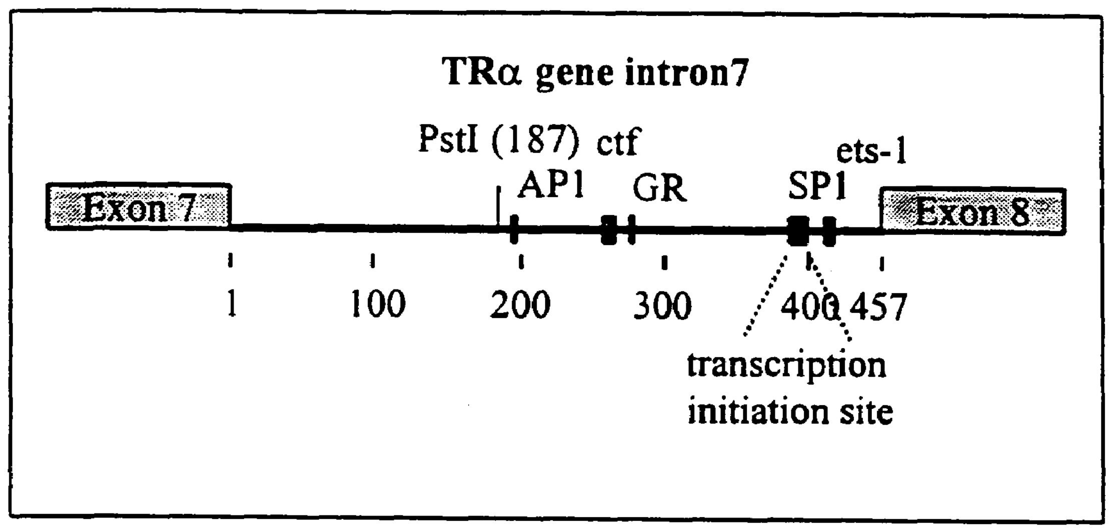
FIG. 6 is a diagram of intron 7 of a TRα gene.

FIG. 6 depicts the organization of intron 7 of the mouse TRα gene. The AP 1, ctf, GR, SP1 and ets-1 sequences of intron 7 have been documented to regulate reporter gene transcription in transient expression assays (Chassande et al., 1997, Mol. Endocrinol. 11: 1278-1290). The isolation of 7-8 kb genomic clones from a mouse 129SV genomic library that span this region is described above.

Figure 7:
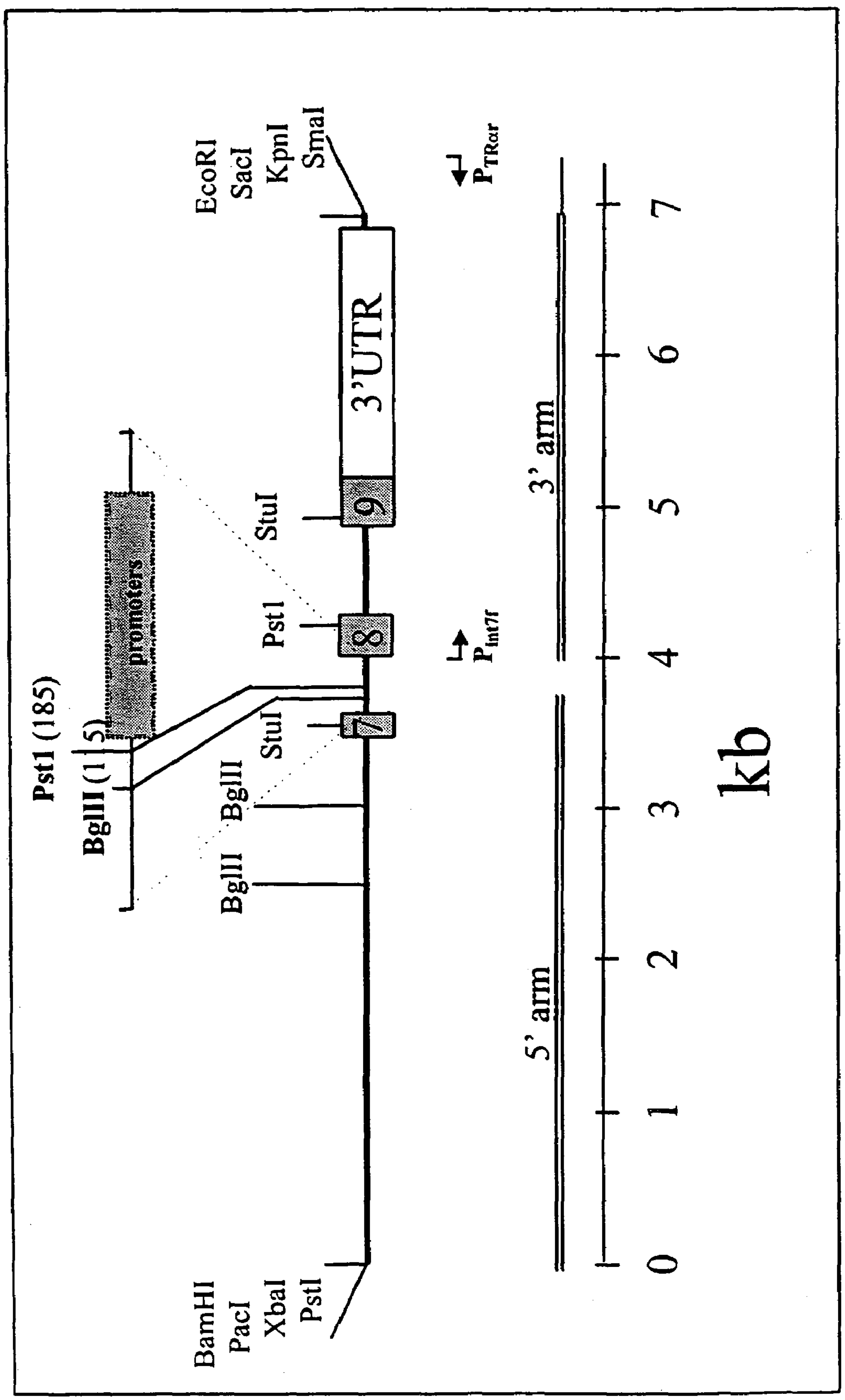
FIG. 7 is a diagram of a scheme for preparing the 5' and 3' arms of a TRα gene for deletion of intron 7 promoters.

Because of the lack of unique restriction sites at the 3' end of the intron 7, the 3' thyroid hormone receptor α gene arm is isolated using PCR-based primers beginning on the 3' end of the SP1 site in intron 7 ($P_{int7f[nt395-414]}PO_4$-GGAGACT-GTGGGGTGTGG; SEQ ID NO: 2). The reverse PCR primer is located in the NEB193 shuttle vector ($P_{TR\alpha r}$ $PO_4$-CCAGTGAATTCGAGCTC-3'; SEQ ID NO: 3) and yields an approximately 3.5 kb fragment. This fragment contains the native intron7/exon 8 splice junction and exon 9 of the thyroid hormone receptor a gene. FIG. 7 illustrates the structure and restriction map of this region as well as the location of the 3' and 5' arms. The 5' arm of the TRα gene is isolated using PstI, yielding a ~4 kb fragment containing the 5' splice junction of intron 7 and the native upstream thyroid hormone receptor a sequences. The 5' and 3' arms are ligated into the targeting vector Pneotklox (S. Jones, University of Massachusetts Medical Center) to generate a TRα5' arm -loxP $neo^r$ loxP-TRα3' arm; the negative selection marker TK is appended to the MCS located at the 3' end of the 3' arm of the TRα gene. Restriction mapping and cycle sequencing is used to confirm construct integrity. LoxP sites bracket the G418 resistance gene allowing elimination of this selection marker from ES cells after homologous recombination by transient expression of Cre-expressing plasmids in recombinant ES cells. Regeneration of a shortened intron 7 lacking any coding sequences will eliminate troublesome effects of intron-based coding sequences on expression of the recombinant TRα gene. Other suitable vectors may be used.

Deletion of TRαExon 10

Figure 8:
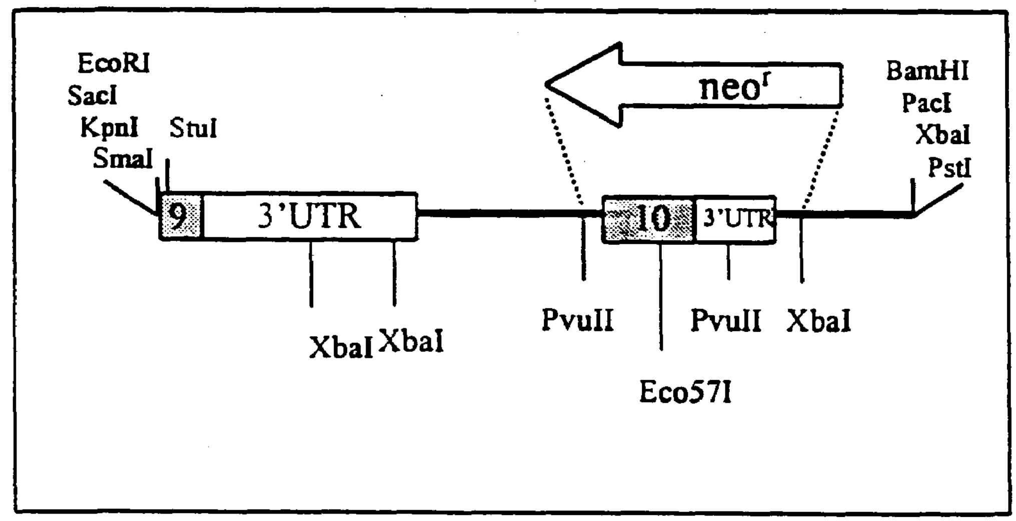
FIG. 8 is a diagram of a scheme for replacing exon 10 of a TRα gene with a $neo^r$ selection gene.

A second knockout construct targets exon 10 of the TRα gene. The rationale for this knockout is based on the finding that the TRs differ only in the C-terminus (encoded in the mouse in exon 10) and ΔTRα1 is not found in myosin V-enriched synaptic vesicles. Thus, ΔTRα2 is the prime candidate as TH-dependent link between the synaptic vesicles to myosin V. Deletion of exon 10 eliminates the ability to produce both full-length, non-T3 binding TRα2 and ΔTRα2. These mice retain expression of the T3-binding thyroid hormone receptors that regulate gene expression and the ΔTRα1, and thus allow examination of the role of ΔTRα2 and full-length TRα2. The TRα clone described above spans this region and the entire sequence of exon 10 is replaced with the $neo^r$ selection gene using standard approaches and appropriate restriction sites. FIG. 8 illustrates the structure and restriction map of this region. It is not necessary in the case of exon 10 deletions to remove the $Neo^r$ selection gene prior to homologous recombination in ES cells.

ES cells are electroporated with Pacd linearized int7 or exon10 targeting constructs, grown, and recombinant ES cells are isolated using both positive ($neo^r$) and negative (TK) selection according to established protocols (e.g., Ausubel et al., supra). Depending on the targeting construct, this results in the selection of $ES^{int7+/-}$ and the $ES^{exon10+/-}$ cells. Restriction fragment polymorphism (RFP) analysis and standard Northern analysis of the candidate recombinant ES cells is used to confirm the pressure of the appropriate TRα gene mutations.

Production and Mouse Husbandry

Injection of targeted ES clones ($ES^{int7+/-}$ and the $ES^{exon11+/-}$) into mouse blastocytes is performed for each mutation in duplicate to insure success in the event that any individual ES clone does not contribute to the germline. Identification of founder mice is performed using standard RFP analysis of tail DNA. As is the case with dilute-lethal heterozygotes, for both the Δintron7+/− and the Δexon10+/− founders, one normal allele is expected to provide a normal phenotype and the progeny of heterozygote breeding should yield typical Mendelian patterns. As seen in the dilute-lethal homozygotes, failure to gain weight, disturbances in motor and sensory function, and most likely death will occur prior to maturation at 21 to 28 days. Expression of the ΔTRs is monitored by Northern blot, and immunoblot analysis of whole brain and myosin V-enriched synaptic vesicles.

Functional analysis of the effect of losing the ΔTRs on actin-based endocytosis is performed using cultured astrocytes prepared from affected and normal progeny. As with the dilute-lethal phenotype, disturbed motor function is a potential indicator of the homozygous phenotype. If such a physical sign is lacking, or as an additional test, astrocytes are prepared from individual progeny and the TH-dependent endocytosis of D2 monitored according to established procedures and procedures described herein.

One use of the transgenic animals described above is that they can be used to evaluate the role of ΔTRαs in whole animal viability and in actin-based endocytosis. Furthermore, such animals can be used to evaluate the role of this non-genomic thyroid hormone effector molecule in synapse function. Such animals can also be used to test the effects of candidate compounds in the absence of a receptor, e.g., on non-thyroid hormone receptor associated effects.

Both ΔTRα1 and ΔTRα2 are expressed in the developing and adult brain. The loss of activity of either or both of these gene products will lead to unproductive or impaired synaptic vesicle recycling and reduced synaptic function.

Example 6

Screening Assays for TRα Ligands that Modulate Actin-Based Endocvtosis

A number of different assays can be used to identify the candidate compounds of the invention. Examples of such assays are below.

Identification of ΔTRα Ligands Using Direct Ligand Binding Assays

One assay principle is based on the ligand-dependent association of vesicles to microfilament bound myosin V. As discussed above, immunoreactive ΔTRα2 appears to be constitutively bound to the extreme C-terminus of myosin V and the addition of specific thyroid hormones (T4 and rT3 but not T3) cause membrane vesicles to bind to the microfilaments. Thus, ligand binding serves to tether a vesicle to the actin-bound myosin V. Deletion studies (supra) have identified the last 22 amino acids of myosin V as the region responsible for tethering the vesicle to myosin V. The use of actin and myosin complexes can be eliminated by directly fixing a ΔTRα to a solid phase or by fixing a peptide derived from the C-terminus of myosin V to a solid phase and allowing the ΔTRα to bind to this specific peptide. Ligand-dependent binding of labeled (e.g., with a fluorescent molecule) vesicles to the immobilized ΔTRα can be monitored directly by high throughput readers that detect the label.

For example, N-tagged (6-his or HA) ΔTRα are fixed to a solid matrix such as a microtiter dish or nitrocellulose membrane by Ni chelation. Alternatively, antisera raised against the epitope tag (6-His, HA or c-myc) can be fixed to the surface using standard procedures and the eiptope tagged ΔTRα adsorbed to the immobilized antibody. The resultant immobilized ΔTRα can be incubated with ligand, flavonoids, arones, thyroid hormone analogs, or other test or candidate compounds in the presence of membrane vesicles containing a covalently integrated fluorescent tag. After washing, the fluorescence intensity remaining on the solid surface is determined. Avidity, potency and competition with thyroid hormones can be tested using this approach.

Vesicle Motion Studies with T4 and rT3

Another assay that can be used in the invention is based on the observation that specific, thyroid hormone-dependent actin-based endocytosis can be visualized in real time in living astrocytes. Analysis of the hormone-dependent internalization of vesicles can be used to evaluate the potency and specificity of specific ΔTRα ligands on actin-based endocytosis in living cells. To perform such assays, for example, astrocytes constitutively expressing a green-fluorescent protein (GFP)-D2 fusion protein are grown in hormone-free medium on cover slips and treated as described in Leonard, 1988, Biochem. Biophys. Res. Comm. 151:1164-1172 and Leonard et al., 1990, J. Biol. Chem. 265: 940-946. Baseline vesicle movement during a 10 minute initial period will be collected using digital imaging microscopy. Next, a candidate compound identified in the ligand binding screening phase is added to the cells. Internalization of fluorescent D2 over a 10 minute period is monitored, and the data collection and three dimensional reconstruction is completed. This assay can provide an analysis of the potency of a candidate compound in initiating actin-based endocytosis. As with the other assays, this assay may also be used to initially identify candidate compounds.

Alternatively, end point assays can be done using the initial and final distribution of fluorescent D2. Instead of D2, other vesicle proteins such as synaptotagmin, synaptophysin can serve as the analyte.

D2 Measurement as a Marker in vivo and in Culture

There is rapid hormone-dependent regulation of the biological half-life of D2 in cAMP-stimulated astrocytes. This actin-based endocytotic event occurs in the brain in vivo and in cAMP-stimulated astrocytes in culture. Direct analysis of the D2 levels in the brain and/or in cultured astrocytes is another biological end-point for evaluating the selectivity, avidity, and potency of candidate compounds (e.g., ΔTRα ligands). This assay is based on the rapid down-regulation of D2 activity after acute hormone treatment of thyroid hormone-deficient rats (Silva and Leonard, 1985, Endocrinol. 116:1627-1635). For example, to perform such an assay in rodents, animals are rendered thyroid hormone deficient by administration of anti-thyroid drugs such as propylthiouracil (PTU) or methylmercaptoimidazole (MMI) for 2 weeks prior to study (Farwell and Dubord-Tomasetti, 1999, Endocrinol. 140:4221-4227). Test ΔTRα ligands are administered either by ip or iv routes and the levels of D2 activity in brain homogenates determined using assays known in the art (Leonard and Rosenberg, 1980, Endocrinol. 107:1376-83; Visser et al., 1982, Proc. Nat. Acad. Sci. USA 79:5080-5084).

D2 activity-based assays can also be performed in cultured cells. For example, in cAMP-stimulated astrocytes grown in serum-free medium, acute thyroid hormone replacement leads to the rapid (within 10-20 minutes) fall in D2 levels (Leonard, 1988, supra; Leonard et al., 1990, supra; Safran et al., 1993, supra). To perform the assay, confluent monolayers of cultured astrocytes are grown in serum-free medium for 24 hours and D2 activity is induced with 1 mM $bt_2cAMP$ and 100 nM hydrocortisone for 16 hours. Candidate ligands are added in increasing concentrations, the cells harvested after 20 minutes, and D2 activity determined.

D2 activity can be determined using known methods. For example, D2 activity is determined by measuring the release of radioiodide from 2 nM [$^{125}$I] 3' or 5'-rT3 in the presence of 20 mM dithiothreitol and 1 mM 6-n-propylthiouracil (PTU) (Leonard, 1988, supra; Leonard et al., 1981, Science 214:571-573; Leonard and Rosenberg, 1978, Endocrinol. 103:2137-2144; Visser et al., 1981, Biochem. Biophys. Res. Comm. 101:1297-304; Visser et al., 1982, supra). Assays are done in a total volume of 100 μl. 20-100 μg of cell or tissue homogenate protein is added to an assay mixture composed of 100 mM potassium phosphate buffer (pH 7.0), 1 mM EDTA, 2 nM [$^{125}$I] 3' or 5'-rT3 (500 cpm/fmol), 20 mM dithiothreitol and 1 mM PTU. After incubation at 37° C. for 20-60 minutes, 50 μl of a stop solution (4 mg/ml BSA and 5 mM PTU) that binds rT3 and prevents re-organification of the released radioiodide is added and the unmetabolized substrate is precipitated with 350 μl of 10% trichloroacetic acid (TCA; w/v). After clarification by centrifugation, the acid soluble extract containing the released radioiodide is passed over a 2 ml bed of cation exchange resin (DOWEX 50W) to remove any unprecipitated rT3 and the flow through fraction is counted in a well-type γ counter.

In vitro Actin Binding Assay: Thyroid Hormone-dependent Binding of p29 Vesicles to the F-actin Cytoskeleton An in vitro binding assay was developed whose principle is based on the hormone dependent redistribution of affinity labeled p29 between the Triton-soluble (vesicle pool) and Triton-insoluble (F-actin cytoskeleton) fractions. The assay was used to examine the hormone dependent relationship between the p29-containing endosome and the F-actin cytoskeleton. Two different pools of astrocytes were prepared. F-lysate provided a fully polymerized F-actin cytoskeleton with its associated myosin V and was prepared by treating thyroid hormone-deficient astrocytes in serum-free medium for 24 hours with 10 μM retinoic acid (Farwell and Leonard, 1992, Endocrinol. 131: 721-728). The other astrocyte pool was used to prepare affinity BrAc [$^{125}$ I]T4-labeled p29 vesicles from thyroid-deficient cells (V-lysate; Farwell et al. 1990, J. Biol. Chem. 265:18546-18553). V-lysates were prepared from cAMP-stimulated astrocytes grown in serum-free media that were labeled with 2 nM BrAc[$^{125}$ I]T4 as described in Farwell et al. (1990, J. Biol. Chem. 265: 18546-18553). Microtubules were eliminated in all cells by treatment with 10 μM colchicine for 30 minutes prior to cell isolation. After pretreatment, cells were scraped from the flask, collected by centrifugation (500×g for 5 minutes), washed with phosphate buffered saline (pH 7.4), and the cell pellets were lysed by two freeze-thaw cycles (Farwell et al., 1990, supra; Farwell et al., 1993, J. Biol. Chem. 268: 5055-5062). Lysates could be stored at −70° C. for up to 4 weeks without loss of biological activity.

To perform actin attachment assays, F- and V-lysates (100 μg cell protein each) were combined on ice, then 10 nM T4, 10 nM rT3, or 10 nM T3 were added, and the mixtures were incubated for 20 minutes at 37° C. After the incubation, the mixtures were chilled on ice for 2 minutes, then Triton X-100® (0.5% v/v, final) was added and the soluble (Triton supernatant, vesicles) and insoluble (Triton pellet, F-actin) fractions were separated by microfuge centrifugation at 4° C. for 5 minutes. The distribution of [$^{125}$ I]-labeled p29 was then determined by SDS PAGE analysis.

This assay permits analysis of the effects of thyroid hormone on the distribution of [$^{125}$ I]-labeled p29 vesicles. In these experiments, comparable amounts of radiolabeled p29 were present in all treatment groups, as judged by the intensity of the lower band of the doublet of radiolabeled proteins at about 30 kDa (Farwell and Leonard, 1989, J.

Biol. Chem. 264:20561-20567). Addition of 10 nM T3 to the mixed cell lysates did not lead to the binding of [$^{125}$I]-labeled p29 to F-actin and more than 90% of the p29 remained in the non-actin bound, Triton-soluble fraction. Addition of 10 nM T4 to the broken cell preparation resulted in the binding of more than 70% of the radiolabeled p29 to the Triton insoluble, F-actin fraction. These data indicate that the T4-dependent binding of the p29 subunit of D2 to the actin cytoskeleton observed in living astrocytes (Farwell et al. 1990, J. Biol. Chem. 265: 18546-18553) is mimicked in broken cell preparations.

These data demonstrate that this in vitro actin binding assay can be used to assay test compounds and candidate compounds and is useful for the present invention.

Binding of p29 to the Actin Cytoskeleton is Calcium, Magnesium, and ATP Dependent The in vitro actin binding assay demonstrated that T4 specifically induced the binding of p29 endosomes to F-actin. To determine whether this is a direct interaction between the vesicle and F-actin or is mediated by other actin-bound proteins, e.g., myosin V, the release of p29 vesicle bound to F-actin by activating a Ca-dependent Mg-ATPase was investigated. Synaptic vesicle-bound myosin V is released from F-actin by activating the Ca-dependent MgATPase found in the actin binding head of myosin V (Prekeris et al, 1997, J. Cell Biol. 137: 1589-1601; Nascimento et al., 1996, J. Biol. Chem. 271:17561-17569). In this experiment, confluent monolayers of astrocytes were grown in serum-free media for 16 hours, then D2 activity was induced with $bt_2cAMP$ and hydrocortisone, and the p29 vesicle was affinity radiolabeled with BrAc[$^{125}$I]T4. Cell lysates containing approximately 50,000 cpm of BrAc[$^{125}$I]T4-labeled p29 were pretreated with 10 nM for 20 minutes at 37° C., followed by an additional 20 minute incubation with 0.1 mM $Ca^{2+}$, 1 mM $Mg^{2+}$, 0.1 mM ATP, or 5 mM EGTA. Triton-insoluble (F-actin bound) pellets were prepared as described herein. Equal volumes of V-lysate containing BrAc[$^{125}$ I]T4-labeled p29 vesicles and F-lysate were mixed and maximal p29 vesicle:F-actin binding was initiated by adding 10 nM T4. Following pre-incubation with T4, the reconstituted lysates were then supplemented with 0.1 mM $Ca^{2+}$, 1 mM $Mg^{2+}$, 0.1 mM ATP, and/or 5 mM EGTA, and incubated for 30 minutes at 37° C. Triton-insoluble (F-actin-bound) pellets were separated from the Triton-soluble (vesicle) fraction by microfuge centrifugation (14,000×g for five minutes) and the distribution of p29 was determined by y-counting, and by SDS-PAGE analysis.

Approximately 80% of the total p29 vesicles added were bound to F-actin at the start of the experiment. Addition of divalent ions ($Ca^{2+}$and $Mg^{2+}$) and ATP resulted in the release of about 70% of the p29 vesicles from F-actin without altering the F-actin content in the Triton pellet. The calcium chelator, EGTA, blocked more than 50% of the $Ca^{2+}$-stimulated, $Mg_2$ATPase-dependent release of p29 from F-actin. Similarly, removing the substrate, ATP, either divalent ion ($Mg^{2+}$, or $Ca^{2+}$) completely blocked the release of p29 vesicles from the actin cytoskeleton. These data show that F-actin-bound, myosin motor protein(s), presumably myosin V, participate in the binding of the p29 vesicle to F-actin.

Example 7

Determination of Dose-Response Relationships of ΔTRα Ligands

Large Scale Screening

Both dose-response relationships and competition assays are determined for likely ΔTRα ligands (candidate compounds) identified, e.g., by initial screens. Increasing concentrations of a candidate compound are added to a fixed concentration of an immobilized ΔTRα and the fluorescent vesicle and the ligand-dependent binding of the analyte vesicles systematically determined. From these data $K_a$ (EC50's) can be determined.

Competition assays for the immobilized ΔTRα with T4, the presumed physiological ligand, are performed by simple radiometric assay. Immobilized ΔTRα is incubated with 1 nM [$^{125}$I]-T4 and increasing concentrations of candidate ΔTRα ligands for 30 to 120 minutes at 4° C. Unbound [$^{125}$I]-T4 is removed by repeated washing and the quantity of [$^{125}$I]-T4 bound to the immobilized ΔTRα determined. Relative potency for the binding site, and specificity of binding can be characterized using these approaches.

Biological Screening

Based on the competitive binding curves and dose-response relationships determined using the simple binding assays described herein, the ability of the candidate compounds, e.g., ΔTRα ligand(s) to initiate actin-based endocytosis, and D2 inactivation is determined using methods known in the art (Leonard et al., 1990, J. Biol. Chem. 265:940-946; Safran et al., 1993, J.Biol. Chem. 268:14224-14229) and described herein.

Example 8

Hormone-induced Synaptic Vesicle (SV) Trafficking in Cerebellar Granule Neurons

All of the major components of hormone-induced vesicle trafficking in astrocytes (actin fibers, myosin V (also referred to as myosin 5a and myo 5a), and recycling vesicles) are also present in nerve terminals. Therefore, the effects of thyroid hormone on synaptic vesicle recycling in the presynaptic nerve terminal were examined using myo5a-dependent synaptic vesicle (SV) recycling in cultured cerebellar granule neurons. In these experiments, rat granule neurons were grown on laminin-coated coverslips in the absence or presence of hormone and synaptic vesicle recycling was examined using FM1-43 (a styryl dye used in the art for studying endocytosis and exocytosis, e.g., in synaptic vesicle uptake and release assays; Molecular Probes, Inc. Eugene, Oreg.). These experiments demonstrated that K+-induced synaptic vesicle loading was under hormonal control. Analysis of the quantity of FM1-43 that was in the reserve pool, i.e., retained by individual nerve terminals after a three minute period of autonomous activity, showed that >80% of the dye was released from granule neurons grown in hormone-free medium. In contrast, granule neurons grown in thyroid hormone supplemented medium released only 15-20% of the FM1-43 after six minutes of incubation and the hormone specificity of retention of FM1-43 in the "reserve pool" was identical to that determined for myo5a-dependent, endocytosis of p29 vesicles (D2p29 vesicles) in astrocytes.

To perform these experiments, cultured cerebellar granule neurons were used to determine if recycling synaptic vesicles showed hormone-induced myo5a-dependent trafficking. Cerebellar granule neurons were examined because thyroid hormone has a profound influence on granule neuron viability during cerebellar maturation (Xiao and Nikodem, 1998, Front. Biosci. 3: A52-57; Rabie et al., 1980, Brain Res. 190:409-414), and because of the effects of the loss of myo5a on synaptic vesicle homeostasis (Bridgman, 1999, J. Cell Biol. 146:1045-1060). Cerebellar granule neurons were isolated from 4 day old rats, seeded at ~100,000 cells/cm$^2$ on p-lysine/laminin-coated coverslips and grown for 7-10 days in BME medium supplemented with 10% (v/v) fetal calf serum. Astrocyte proliferation was suppressed by treating the cultures on day three and day six with the anti-mitotic, Ara-C. The cultures contained multi-processed, neurofilament positive neurons and a few polygonal astrocytes.

Experiments were conducted to determine whether synaptic vesicle endocytosis could be altered by the hormone status of the neuron. Recycling synaptic vesicles were labeled with FM1-43. Synaptic vesicle recycling was initiated by depolarization with 50 mM KCl for 60 seconds. Cells were then rapidly washed free of KCl and the endocytic synaptic vesicles were then loaded by a 60 second incubation with 15 mM FM1-43 in the absence of KCl. The dye was then removed and the number, intensity and retention of the FM1-43 in random nerve terminals immediately after washing and after six minutes of autonomous activity were analyzed in paraformaldehyde fixed cells (Ryan, 1999, J. Neurosci.: 19:1317-1323). Fluorescence in single nerve terminals (ROI=7×7 pixels) and in an adjacent segment of the neuronal fiber were measured for 40-45 individual nerve terminals. Images were captured using Nikon Eclipse E600 microscope, fitted with a 40×/0.75 Plan Fluor objective and a SPOT RT Color digital camera. Fluorescence intensity was determined using NIH Image software. The total FM1-43 fluorescence in a nerve terminal represents the sum of the dye-loaded synaptic vesicles in the readily releasable and the reserve pools.

Under the labeling conditions described above, recycling vesicles in both neurons and astrocytes took up the dye; however, the neurons showed the punctate pattern of staining characteristic of functional synapses, i.e., bright spots distributed along long fibers and on the surface of the nerve cell body. By allowing recurrent activity, the FM1-43 filled synaptic vesicles present in the readily releasable pool will be progressively depleted. Thus, the residual FM1-43 found in nerve terminals after six minutes of autonomous activity should represent the recycled synaptic vesicles that were shuttled to the reserve pool. By measuring the total FM1-43 content in random nerve terminals immediately after loading and at 30 second intervals for six minutes of spontaneous activity, the influence of hormones on the distribution of recycling synaptic vesicles between the readily releasable and reserve pools was estimated.

The data in FIG. 10 show the effects of T3 and T4 on the FM1-43 content in nerve terminals of cultured cerebellar neurons immediately after loading and after three minutes of spontaneous activity. No differences in the uptake of FM1-43 were observed in the three experimental conditions tested indicating that hormones did not affect the initial recovery of synaptic vesicles from the plasma membrane. After three minutes of spontaneous activity, >80% of the endocytosed FM1-43 was released in both the no hormone and the T3-treated neurons. This suggests that most of the FM1-43 filled synaptic vesicles had remained in the readily releasable pool. In contrast, granule neurons acutely treated with T4 retained >90% of the endocytosed FM1-43 after three minutes of spontaneous stimulation. These data suggest that T4, but not T3, promoted the centripetal redistribution of the newly recaptured synaptic vesicles from the readily releasable pool to the reserve pool, just as was found for endocytosis of recycling vesicles in astrocytes.

Example 9

Dynamic Studies of Synaptic Vesicle Recycling

To examine the dynamics of synaptic vesicle recycling and the role of thyroid hormone in the process, neurons expressing selected dominant negative myo5a constructs were used.

Granule neurons were grown for 7 days and rendered hormone free by growth in serum-free medium as detailed above. Coverslips were then placed in a perfusion chamber, mounted on the stage of a laser scanning confocal microscope and perfused at 1 ml/min at 25° C. with perfusion buffer (119 mM NaCl, 2.5 mM KCl, 2 mM $CaCl_2$, 2 mM $MgCl_2$, 25 mM HEPES (pH 7.4), 30 mM glucose, and 50 mM AP-5). The effects of different hormones on synaptic vesicle trafficking were then determined. In brief, neurons were perfused with labeling buffer consisting of perfusion buffer containing BSA buffered 10 nM T4, 10 nM T3, or 10 nM rT3; 15 mM FM1-43; and 50 mM KCl for one minute. Depolarizing KCl was then removed from the perfusion buffer and the cells were exposed to FM1-43 for an additional 30 seconds to insure complete loading of recycling synaptic vesicles. Loaded cells were then washed free of dye and the cells were perfused for ten minutes at rest.

Images of a single field of neuronal fibers were then taken immediately before adding a second depolarizing solution (perfusion buffer containing 50 mM KCl) and at one and two minutes after beginning the continuous stimulation by 50 mM KCl. Thirty to forty-five individual FM1-43 labeled nerve terminals were identified in the baseline images (taken prior to depolarization) and the change in fluorescence (DF) for each nerve terminal determined at the one and two minute time points. FIGS. 11A and 11B show the results of analysis of the hormone specificity of synaptic vesicle trafficking (FIG. 11A) and the influence of individual myo5a mutants (FIG. 11B) on synaptic vesicle transport in granule neurons.

As observed in the synaptic vesicle labeling study of astrocytes, hormones that initiate actin-based endocytosis of recycling vesicles in astrocytes (i.e., T4 and rT3) also promote the retention of FM1-43 labeled synaptic vesicles even during a maximal depolarizing stimulus. Assuming first order kinetics for the release of endocytosed FM1-43 during continuous stimulation, both T4 and rT3 decreased the rate of FM1-43 release by 75% ($t_{1/2}$=182 seconds vs. 44 seconds in no hormone controls). This is in contrast to T3 which had no effect on the retention of recycling synaptic vesicles ($t_{1/2}$=44 seconds). These results indicate that the delivery of recycling synaptic vesicles to the nonreleasable or reserve pool in the presynaptic nerve terminals of cerebellar granule cells shows the same hormone specificity as the recycling vesicles in rat astrocytes.

These data show that candidate compounds of the invention that are, e.g., discovered using astrocyte assays, can also be effective in neuronal cells.

In a second study, the dynamics of synaptic vesicle recycling in individual nerve terminals using the loading-rest-stimulation paradigm of Ryan (Ryan et al, 1996, J. Cell Biol. 134:1219-1227; Ryan, 1999, J. Neurosci. 19:1317-1323; Ryan et al, 1993, Neuron 11: 713-724; Sankaranarayanan and Ryan, 2000, Nat. Cell Biol. 2:197-204) were studied.

To evaluate the role of myo5a in synaptic vesicle transport, three different myo5a constructs were introduced into the neurons by replication-deficient adenoviral vectors ($\Delta$myo5a$^{tail}$(MyoV$^{tail}$), $\Delta$myo5a$^{c\text{-}term}$(MyoV$^{1830}$)and $\Delta$Myo5a$^{CC}$(MyoV$^{cc}$) see FIG. 5) as described above. The granule neurons were readily infected with Ad5 constructs as was observed for cultured rat astrocytes. Neurons were infected with purified Ad5-constructs (MOI=10) 48 hours prior to the synaptic vesicle trafficking study, and allowed to recover in hormone (T4) supplemented medium. As detailed in FIG. 11B, over-expression of the ~88kDa myo5a$^{tail}$ (myo5a$^{tail}$) completely blocked the hormone-dependent retention of FM1-43 loaded synaptic vesicles, while expression of the coiled-coil region ($\Delta$myo5a$^{CC}$) had little, if any, effect on the retention of recycled synaptic vesicles in nerve terminals exposed to continuous depolarization. Expression of the vesicle-binding domain (VBD, $\Delta$myo5a$^{C\text{-}term}$) had a modest but statistically significant effect and increased the $t_{1/2}$ of FM1-43 retention by 50%. This modest influence of the VBD mutant on synaptic vesicle retention is likely to be due to the loss of the kinesin-binding domain that limits its delivery to nerve terminals.

These results confirm the specific hormone-dependent delivery of FM1-43-loaded synaptic vesicles to a "reserve pool" and show that over-expression of the dominant negative myo5a$^{tail}$ specifically blocks FM1-43 retention by these neurons. Thus, it appears that myo5a delivers the recycled synaptic vesicles to a reserve pool and that these synaptic vesicles can be mobilized under prolonged stimulation. These data point directly to myo5a as the motor responsible for synaptic vesicle recycling in cerebellar granule neurons and indicate that this process is similar to the myo5a-dependent vesicle trafficking in astrocytes. These results suggest that the endocytosed synaptic vesicle in the presynaptic nerve terminal binds to the vesicle binding domain of the myo5a tail and is then delivered to the reserve pool, where synapsin-dependent crosslinks immobilize the synaptic vesicle and stabilize the reserve pool. Without the myo5a-dependent vectoral delivery of the synaptic vesicles to the reserve pool, a key communication pathway is lost and this interrupted reciprocity between the two pools of synaptic vesicles leads to synaptic fatigue.

These data show that myo5a is a target for identifying compounds that modulate synaptic vesicle trafficking. The data also suggest that transport of recycling synaptic vesicles to the reserve pool in the nerve terminal can be modulated by hormones, therefore, analogs and antagonists of such hormones can be useful for modulating synaptic vesicle transport, particularly synaptic vesicle trafficking between the active and the reserve zones of synaptic vesicle pools. Such hormones, analogs, and antagonists are useful for treating disorders or conditions of the nervous system that can be treated by altering synaptic vesicle trafficking, thus affecting the synthesis, storage, release, or degradation of a neurotransmitter.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a candidate compound that modulates mammalian ΔTRα2 polypeptide activity, the method comprising:

a) obtaining a mammalian ΔTRα2 polypeptide b) contacting the ΔTRα2 polypeptide with a test compound, and c) assaying for binding of the test compound to the ΔTRα2 polypeptide, wherein binding indicates that the test compound is a candidate compound.

2. A method of identifying a candidate compound that modulates mammalian ΔTRα2 polypeptide activity, the method comprising:

a) obtaining a mammalian ΔTRα2 polypeptide bound to a ΔTRα2 ligand, b) contacting the-ΔTRα2 polypeptide bound to the ΔTRα2 ligand with a test compound, and c) measuring the displacement of the ΔTRα2 ligand from the ΔTRα2 polypeptide, wherein displacement indicates that the test compound is a candidate compound that modulates ΔTRαt2 polypeptide activity.

3. A method of identifying a candidate compound that modulates mammalian ΔTRα2 polypeptide activity, the method comprising:

a) obtaining a test sample containing a cell expressing a mammalian ΔTRα2 polypeptide, b) incubating the test sample with a test compound, and c) assaying the test sample containing the test compound for an alteration in type II 5' deiodinase (D2) activity, such that a test compound that alters D2 activity when compared to a test sample that was not incubated with the test compound is a candidate compound.

4. The method of claim 3, wherein the test compound decreases the amount of D2 activity.

5. A method of identifying a candidate compound that modulates mammalian ΔTRα2 polypeptide activity, the method comprising:

a) obtaining a test sample containing a mammalian ΔTRα2 polypeptide, b) performing an actin binding assay with the test sample in the presence of a test compound, such that a test compound that alters the binding of p29 vesicles to F-actin when compared to a test sample that was not incubated with the test compound is a candidate compound.

6. The method of claim 1, wherein the test compound is a flavone.

7. The method of claim 2, wherein the test compound is a flavone.

8. The method of claim 3, wherein the test compound is a flavone.

9. The method of claim 5, wherein the test compound is a flavone.

10. The method of claim 1, wherein the test compound is an aurone.

11. The method of claim 2, wherein the test compound is an aurone.

12. The method of claim 3, wherein the test compound is an aurone.

13. The method of claim 5, wherein the test compound is an aurone.

14. The method of claim 1, wherein the test compound is a T4 analog.

15. The method of claim 2, wherein the test compound is a T4 analog.

16. The method of claim 3, wherein the test compound is a T4 analog.

17. The method of claim 5, wherein the test compound is a T4 analog.

18. The method of claim 1, wherein the ΔTRα2 polypeptide comprises an amino acid sequence that is at least 95% identical to the full length of SEQ ID NO:5 and can bind myosin.

19. The method of claim 2, wherein the ΔTRα2 polypeptide comprises an amino acid sequence that is at least 95% identical to the full length of SEQ ID NO:5 and can bind myosin.

20. The method of claim 3, wherein the ΔTRα2 polypeptide comprises an amino acid sequence that is at least 95% identical to the full length of SEQ ID NO:5 and can bind myosin.

21. The method of claim 5, wherein the ΔTRα2 polypeptide comprises an amino acid sequence that is at least 95% identical to the full length of SEQ ID NO:5 and can bind myosin.

* * * * *

UNITED STATES PATENT AND TRADEMARK OFFICE

CERTIFICATE OF CORRECTION

PATENT NO. : 7,374,890 B2
APPLICATION NO. : 10/822591
DATED : May 20, 2008
INVENTOR(S) : Jack L. Leonard and Alan P. Farwell It is certified that error appears in the above-identified patent and that said Letters Patent is hereby corrected as shown below:

Title Page 1, “OTHER PUBLICATIONS,” column 1, lines 13-16, delete the first occurrence of the Chassande et al., 1997, reference.

Title Page 1, “OTHER PUBLICATIONS,” column 2, line 2, delete “Endrocrinol.” and replace with --Endocrinol.--

In column 37, line 25, delete “the-ΔTRα2” and replace with --the ΔTRα2--; and in line 30, delete “ΔTRαt2” and replace with --ΔTRα2--

Signed and Sealed this

Twenty-third Day of September, 2008

JON W. DUDAS
*Director of the United States Patent and Trademark Office*